(12) United States Patent
Hirata et al.

(10) Patent No.: US 7,758,470 B2
(45) Date of Patent: Jul. 20, 2010

(54) EXERCISE MANAGEMENT SYSTEM

(75) Inventors: Takashi Hirata, Wako (JP); Ken Yasuhara, Wako (JP); Kei Shimada, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 99 days.

(21) Appl. No.: 12/295,755

(22) PCT Filed: Mar. 26, 2007

(86) PCT No.: PCT/JP2007/056195

§ 371 (c)(1),
(2), (4) Date: Oct. 2, 2008

(87) PCT Pub. No.: WO2007/116682

PCT Pub. Date: Oct. 18, 2007

(65) Prior Publication Data

US 2009/0227424 A1 Sep. 10, 2009

(30) Foreign Application Priority Data

Apr. 6, 2006 (JP) .............................. 2006-105181

(51) Int. Cl.
*A63B 71/00* (2006.01)
(52) U.S. Cl. .................. 482/7; 482/1; 482/8; 482/9; 482/901; 434/247
(58) Field of Classification Search ............... 482/1–9, 482/51, 54, 900–902; 434/247, 250, 255; 600/300
See application file for complete search history.

(56) References Cited

U.S. PATENT DOCUMENTS

| 6,632,158 B1* | 10/2003 | Nashner | 482/8 |
| 2007/0060446 A1* | 3/2007 | Asukai et al. | 482/8 |
| 2007/0219059 A1* | 9/2007 | Schwartz et al. | 482/8 |
| 2008/0096726 A1* | 4/2008 | Riley et al. | 482/8 |

FOREIGN PATENT DOCUMENTS

| EP | 1 547 567 | 6/2005 |
| WO | 00/28927 | 5/2000 |
| WO | 02/15819 | 2/2002 |

* cited by examiner

*Primary Examiner*—Glenn Richman
(74) *Attorney, Agent, or Firm*—Rankin, Hill & Clark LLP

(57) ABSTRACT

A system for managing exercise of an animal such as a human being so that the animal can be trained to move with an appropriate scale and rhythm while harmonizing the motion of the animal with the operations of two devices which induce the motion of the animal in different manners, is provided. According to the exercise management system (1) of the present invention, the speed of the walking motion of the user is adjusted by an operation of a treadmill (first motion induction device) (10). The user's walking motion is induced with the motion scale being adjusted with a rhythm harmonized with the motion rhythm of the animal by an operation of a walking motion induction device (second motion induction device) (20). At this time, the operation of the walking motion induction device (20) is controlled based on the walking speed v (walking rate p, as required). Accordingly, it is possible to train the user so that the user walks with an appropriate scale and rhythm, while realizing harmonization between the walking motion of the user, the operation of the treadmill (10), and the operation of the walking motion induction device (20).

11 Claims, 10 Drawing Sheets

LOW  MUSCLE GROUP  HIGH
ACTIVITY

LOW  MUSCLE GROUP  HIGH
ACTIVITY

EXERCISE MANAGEMENT SYSTEM

TECHNICAL FIELD

The present invention relates to a system and method for managing exercise of an animal, and a program for providing a computer with the management function.

BACKGROUND ART

There have been proposed techniques for walking training of a user, wherein the speed of a treadmill is set so that the walking speed and the step width become appropriate in consideration of the physical strength and physical conditions of the user (see, for example, Japanese Patent Application Laid-Open Nos. 2001-238982 and 2001-346906).

DISCLOSURE OF THE INVENTION

Problem to be Solved by the Invention

In the case where a device is attached to the user for applying a force to the user's body to induce (or assist) the motion of the user's legs, however, it has not been considered to train the user in walking so that the user walks at an appropriate step width and the like, while harmonizing the movements of the user, the treadmill, and the device.

In view of the foregoing, it is an object of the present invention to provide a system and method for managing exercise of an animal such as a human being, which enables training of the animal so that the animal moves with an appropriate scale and rhythm, while realizing harmonization between the motion of the animal and the movements of two devices which induce the motion of the animal in different manners, and a program which provides the management function to a computer.

Means for Solving the Problem

An exercise management system according to a first invention to achieve the above object includes: a motion variable measuring unit which measures a motion variable representing one or both of a motion scale and a motion rhythm of the animal based on an operating speed of a first motion induction device, motion of the animal being induced by an operation of the first motion induction device; and a control unit which controls an operation of a second motion induction device based on the motion variable measured by the motion variable measuring unit, the second motion induction device inducing the motion of the animal while adjusting the motion scale of the animal with a rhythm harmonized with the motion rhythm of the animal.

According to the exercise management system of the first invention, the motion of the animal is induced, with the motion speed of the animal being adjusted by the operation of the first motion induction device, and with the motion scale being adjusted with a rhythm that is harmonized with the motion rhythm of the animal by the operation of the second motion induction device. At this time, the operation of the second motion induction device is controlled based on the motion variable representing one or both of the motion scale and the motion rhythm of the animal whose motion is induced by the operation of the first motion induction device. The motion variable is measured based on the operating speed of the first motion induction device, which improves the measurement accuracy thereof. This makes it possible to cause the animal to continue the motion, while adjusting the relationship between the motion scale and the motion rhythm of the animal appropriately, by keeping it to a target relationship, for example. As a result, it is possible to train the animal by causing the animal to move with an appropriate scale and rhythm (or target scale and rhythm), while realizing harmonization between the motion of the animal and the operations of the first and second motion induction devices.

Further, an exercise management system according to a second invention is characterized in that, in the exercise management system of the first invention, the motion variable measuring unit includes a first motion variable measuring unit which measures a first motion variable based on a speed of circular movement of a circular motion body provided in the first motion induction device, the first motion variable being the motion variable which represents a speed of the motion of the animal, the motion of the animal being induced in a direction opposite from a direction of the circular movement of the circular motion body as the animal is in contact with the circular motion body.

According to the exercise management system of the second invention, with the motion of the animal being induced by the operation of the first motion induction device, the operation of the second motion induction device is controlled based on the "first motion variable" which represents the speed of the motion of the animal (determined based on the motion scale and motion rhythm of the animal). The first motion variable is measured based on the speed of the circular movement of the circular motion body of the first motion induction device, which improves the measurement accuracy thereof. Accordingly, it is possible to cause the animal to continue the motion while adjusting the relationship between the motion scale and the motion rhythm of the animal as appropriate, by keeping it to a target relationship or the like.

Further, the circular motion body provided in the first motion induction device is caused to perform circular movement, to induce the animal which is in contact with the circular motion body to move in the direction opposite from the direction of the circular movement. The "circular motion body" may be: an endless belt looped over a plurality of rollers; a spherical body or oval sphere rotated about an axis passing the center or a point offset from the center; a tubular body such as a cylinder or square pole rotating about a central axis or an axis offset from and parallel to the central axis; or a block of substance rotated about an arbitrary axis. As the movement of the animal or its body part in accordance with its motion is cancelled out by the circular movement of the endless circular motion body, training of the motion of the animal becomes possible even in a relatively small place, only if there is a space for installing the first motion induction device.

Further, an exercise management system according to a third invention is characterized in that, in the exercise management system of the second invention, the first motion variable measuring unit measures a speed of walking or running motion of the animal as the first motion variable, based on a driven speed of an endless bell serving as the circular motion body looped over a plurality of rollers provided in a treadmill serving as the first motion induction device, the walking or running motion of the animal being induced in a direction opposite from a direction of circular movement of the endless belt as the animal is in contact with the endless belt.

According to the exercise management system of the third invention, the operation of the second motion induction device is controlled based on the walking or running speed (first motion variable) of the animal whose walking or running motion is induced by the operation of the treadmill (first motion induction device). The walking speed is measured based on the driven speed of the endless belt (circular motion body) of the treadmill, which improves the measurement accuracy thereof. Accordingly, it is possible to cause the animal to continue the walking or running motion, while appropriately adjusting the relationship between the step width (motion scale) and the walking rate (motion rhythm) of the animal, by keeping it to a target relationship or the like.

Further, the endless belt (circular motion body) of the treadmill (first motion induction device) is caused to perform circular movement to induce the walking or running in the direction opposite from the direction of the circular movement of the endless belt. This ensures cancellation of the movement of the animal with the walking or running motion by the rotation of the endless belt, thereby enabling walking and running training of the animal in a relatively small place, only with a space for installing the first motion induction device.

Further, an exercise management system according to a fourth invention is characterized in that, in the exercise management system of the first invention, the motion variable measuring unit includes a second motion variable measuring unit which measures a second motion variable based on a pattern of change of a force of interaction between the animal and the first motion induction device, the second motion variable being the motion variable which represents one or both of amplitude and period of periodic motion of the animal, the periodic motion of the animal being induced by the operation of the first motion induction device and the animal, and the control unit controls the operation of the second motion induction device based on the second motion variable measured by the motion variable measuring unit.

According to the exercise management system of the fourth invention, the operation of the second motion induction device is controlled based on the "second motion variable" which represents the motion rhythm of the animal whose motion is induced by the operation of the first motion induction device. The second motion variable is measured based on the pattern of change over time of the force of interaction between the animal and the first motion induction device, which improves the measurement accuracy thereof. Accordingly, it is possible to cause the animal to continue the motion, while appropriately adjusting the relationship between the motion scale and the motion rhythm of the animal, by keeping it to a target relationship or the like.

Further, an exercise management system according to a fifth invention is characterized in that, in the exercise management system of the fourth invention, the second motion variable measuring unit measures a walking rate of the animal as the second motion variable, based on a pattern of change over time of a pressure that is applied by the animal to a footplate which supports an endless belt looped over a plurality of rollers provided in a treadmill serving as the first motion induction device.

According to the exercise management system of the fifth invention, the operation of the second motion induction device is controlled based on the walking rate (second motion variable) of the animal which is induced by the operation of the treadmill (first motion induction device). Every time the animal lands on the endless belt of the treadmill during the walking or running motion, the pressure is applied to the footplate supporting the belt. Thus, the walking rate is measured based on the pattern of change over time of this pressure, resulting in improved measurement accuracy. Accordingly, it is possible to cause the animal to continue the walking or running motion, while appropriately adjusting the relationship between the step width (motion scale) and the walking rate (motion rhythm) of the animal, by keeping it to a target relationship or the like.

Further, the endless belt (circular motion body) of the treadmill (first motion induction device) is caused to perform circular movement to induce the walking or running motion of the animal in the direction opposite from the direction of the circular movement. As the movement of the animal by the walking or running motion is cancelled out by the rotation of the endless belt, training of the walking and running motions of the animal is possible even in a relatively small place, only if there is a space for installing the first motion induction device.

Further, an exercise management system according to a sixth invention is characterized in that, in the exercise management system of the first invention, the motion variable measuring unit includes a first motion variable measuring unit which measures a first motion variable as the motion variable and a second motion variable measuring unit which measures a second motion variable as the motion variable, the first motion variable corresponding to a moving speed of the animal, the second motion variable corresponding to a step width or walking rate of the animal, and the control unit controls the operation of the second motion induction device so that a walking ratio matches a target walking ratio, the walking ratio being either a ratio of a square of the step width as the second motion variable with respect to the moving speed as the first motion variable, or a ratio of the speed as the first motion variable with respect to a square of the walking rate as the second motion variable.

According to the exercise management system of the sixth invention, it is possible to train the animal by causing the animal to walk or run at an appropriate walking ratio, while realizing harmonization between the walking or running motion of the animal and the operations of the first and second motion induction devices.

Further, an exercise management system according to a seventh invention is characterized in that, in the exercise management system of the first invention, the control unit includes: a motion oscillator measuring unit which measures first and second motion oscillators as parameters that periodically change in accordance with the motion of the animal; a first oscillator generating unit which inputs the first motion oscillator measured by the motion oscillator measuring means as an input oscillation signal to a first model which generates an output oscillation signal that changes over time at an angular velocity determined based on a natural angular velocity by mutual entrainment with the input oscillation signal, to generate a first oscillator as the output oscillation signal; a natural angular velocity setting unit which sets a new natural angular velocity based on a phase difference between the motion oscillator measured by the motion oscillator measuring unit and the first oscillator generated by the first oscillator generating unit; a second oscillator generating unit which inputs the second motion oscillator measured by the motion oscillator measuring means as an input oscillation signal to a second model which generates, based on the input oscillation signal, an output oscillation signal that changes over time at an angular velocity determined based on the natural angular velocity set by the natural angular velocity setting means, to generate a second oscillator as the output oscillation signal; and an induction oscillator generating unit which generates an induction oscillator specifying a scale and rhythm of the operation of the second motion induction device, based on the motion variable measured by the motion variable measuring unit in addition to the second oscillator generated by the second oscillator generating unit.

According to the exercise management system of the seventh invention, mutual adaptation is established between the motion rhythm of the animal, which is induced by the operations of the first and second motion induction devices, and the operation or motion induction rhythm of the second motion induction device. Accordingly, it is possible to train the animal to cause it to move with an appropriate scale and rhythm, while realizing harmonization between the motion of the animal and the operations of the first and second motion induction devices.

Further, an exercise management system according to an eighth invention is characterized in that, in the exercise management system of the seventh invention, the motion oscillator measuring unit measures a third motion oscillator representing a motion scale of the animal, and the induction oscillator generating unit generates an induction oscillator including a first induction oscillator which represents an elastic force of a virtual elastic element for inducing the motion of the animal to cause the third motion oscillator measured by the motion oscillator measuring unit to approach a target value set in accordance with a target motion scale of the animal, based on a motion variable measured by the motion variable measuring unit in addition to the second oscillator generated by the second oscillator generating unit and the natural angular velocity newly set by the natural angular velocity setting unit.

According to the exercise management system of the eighth invention, the motion of the animal is induced so that the motion scale of the animal approaches the target scale by the first induction oscillator representing the elastic force of the virtual elastic element. The first induction oscillator is generated based on the natural angular velocity and the motion variable. The "natural angular velocity" is set as appropriate from the standpoint of matching the motion rhythm of the animal with the target rhythm. The "motion variable" represents the state of motion of the animal. Thus, as the motion of the animal is induced by the induction oscillator including the first induction oscillator, it is possible to train the animal by causing the animal to move with an appropriate scale and rhythm, while realizing harmonization between the motion of the animal and the operations of the first and second motion induction devices.

Further, an exercise management system according to a ninth invention is characterized in that, in the exercise management system of the eighth invention, the motion oscillator measuring unit measures the second motion oscillator as the third motion oscillator.

According to the exercise management system of the ninth invention, the second oscillator is generated based on the third motion oscillator (=second motion oscillator) representing the motion scale of the animal. Further, the first induction oscillator is generated for bringing the third motion oscillator close to the target value based on the second oscillator.

Further, an exercise management system according to a tenth invention is characterized in that, in the exercise management system of the eighth invention, the motion oscillator measuring unit measures a motion rhythm of the animal as a fourth motion oscillator, and the induction oscillator generating unit generates the induction oscillator including a second induction oscillator which represents a damping force of a virtual damping element for inducing the motion of the animal to suppress an increase in absolute value of the third motion oscillator, based on a motion variable measured by the motion variable measuring unit, in addition to the second oscillator generated by the second oscillator generating unit, the natural angular velocity set by the natural angular velocity setting unit, and the fourth motion oscillator measured by the motion oscillator measuring unit.

According to the exercise management system of the tenth invention, the motion of the animal is induced to prevent deviation of the motion scale of the animal from the target scale by the second induction oscillator representing the damping force of the virtual damping element. The second induction oscillator is generated based on the natural angular velocity and motion variable, as is the first induction oscillator. The "natural angular velocity" is set as appropriate from the standpoint of causing the user's motion rhythm to match the target rhythm. The "motion variable" represents one or both of the motion scale and the motion rhythm of the animal. Therefore, as the motion of the animal is induced by the induction oscillator including the second induction oscillator, it is possible to train the animal by causing the animal to move with an appropriate scale and rhythm, while realizing harmonization between the motion of the animal, the operation of the first motion induction device, and the operation of the second motion induction device.

Further, an exercise management system according to an eleventh invention is characterized in that, in the exercise management system of the tenth invention, the motion oscillator measuring unit measures the first motion oscillator as the fourth motion oscillator.

According to the exercise management system of the eleventh invention, the first oscillator is generated based on the fourth motion oscillator (=first motion oscillator) representing the motion rhythm of the animal. Further, the natural angular velocity is set based on the first oscillator, and the second induction oscillator for suppressing an increase in absolute value of the third motion oscillator is generated based on the natural angular velocity.

Further, an exercise management system according to a twelfth invention is characterized in that, in the exercise management system of the seventh invention, in the case where a magnitude of periodical change of the first or second motion oscillator measured by the motion oscillator measuring unit exceeds a threshold value, the second oscillator generating unit generates the second oscillator which oscillates at an angular velocity determined based on one or both of an angular velocity of the first or second motion oscillator measured by the motion oscillator measuring unit and an angular velocity of the first oscillator generated by the first oscillator generating unit, instead of the natural angular velocity set by the natural angular velocity setting unit.

According to the exercise management system of the twelfth invention, even if the motion rhythm of the animal changes abruptly, the motion of the animal can be induced at an appropriate rhythm in accordance with the changed motion rhythm. Accordingly, it is possible to train the animal by causing the animal to move with an appropriate scale and rhythm, while realizing harmonization between the motion of the animal and the operations of the first and second motion induction devices.

Further, an exercise management system according to a thirteenth invention is characterized in that, in the exercise management system of the first invention, the control unit includes: a motion oscillator measuring unit which measures the motion oscillators according to movements of two different body parts of the animal as the first and second motion oscillators; a first oscillator generating unit which inputs the first motion oscillator measured by the motion oscillator measuring means as an input oscillation signal to a first model which generates an output oscillation signal that changes over time at an angular velocity determined based on a natural angular velocity by mutual entrainment with the input oscillation signal, to generate a first oscillator as the output oscillation signal; a natural angular velocity setting unit which newly sets the natural angular velocity based on a phase difference between the first motion oscillator measured by the motion oscillator measuring unit and the first oscillator generated by the first oscillator generating unit; a second oscillator generating unit which inputs the second motion oscillator measured by the motion oscillator measuring means as an input oscillation signal to a second model which generates an output oscillation signal that changes over time at an angular velocity determined based on the natural angular velocity newly set by the natural angular velocity setting means, to generate a second oscillator as the output oscillation signal; and an induction oscillator generating unit which generates an induction oscillator specifying a scale and rhythm of the operation of the second motion induction device, based on the motion variable measured by the motion variable measuring unit in addition to the second oscillator generated by the second oscillator generating unit.

According to the exercise management system of the thirteenth invention, the motion of the animal may be induced so that the motion rhythm of the animal approaches the target motion rhythm, while harmonizing the motion rhythms of the different body parts of the animal with the rhythm of inducing the motions. Accordingly, it is possible to train the animal by causing the animal to move with an appropriate scale and rhythm, while realizing harmonization between the motion of the animal and the operations of the first and second motion induction devices.

A method according to a fourteenth invention to achieve the above-described object is a method for managing exercise of an animal, which includes the steps of: measuring a motion variable representing one or both of a motion scale and a motion rhythm of the animal based on an operating speed of a first motion induction device, the motion of the animal being induced by an operation of the first motion induction device; and controlling an operation of a second motion induction device based on the measured motion variable, the second motion induction device inducing the motion of the animal while adjusting the motion scale of the animal with a rhythm harmonized with the motion rhythm of the animal.

According to the exercise management method of the fourteenth invention, as in the exercise management system of the first invention, it is possible to train the animal by causing the animal to move with an appropriate scale and rhythm, while realizing harmonization between the motion of the animal and the operations of the first and second motion induction devices.

A program according to a fifteenth invention to achieve the above-described object is a program for causing a computer to function as a system for managing exercise of an animal, wherein the program causes the computer to function as the system including: a motion variable measuring unit which measures a motion variable representing one or both of a motion scale and a motion rhythm of the animal based on an operating speed of a first motion induction device, motion of the animal being induced by an operation of the first motion induction device; and a control unit which controls an operation of a second motion induction device based on the motion variable measured by the motion variable measuring unit, the second motion induction device inducing the motion of the animal while adjusting the motion scale of the animal with a rhythm harmonized with the motion rhythm of the animal.

According to the exercise management program of the fifteenth invention, it is possible to cause the computer to function as the system which trains the animal by causing the animal to move with an appropriate scale and rhythm, while realizing harmonization between the motion of the animal and the operations of the first and second motion induction devices. It is noted that the functions may be provided to a single computer, or to a plurality of computers in a distributed manner.

BEST MODE FOR CARRYING OUT THE INVENTION

Embodiments of the exercise management system, exercise management method, and exercise management program of the present invention will be described with reference to the drawings. Hereinafter, subscripts L and R will be attached to parameters to make a distinction between left and right for walker's legs or the like, although the subscripts L and R are omitted in the case where such distinction is not particularly necessary, for simplicity of notation.

The configuration of the exercise management system of the present invention will now be described with reference to FIG. 1.

Figure 1:
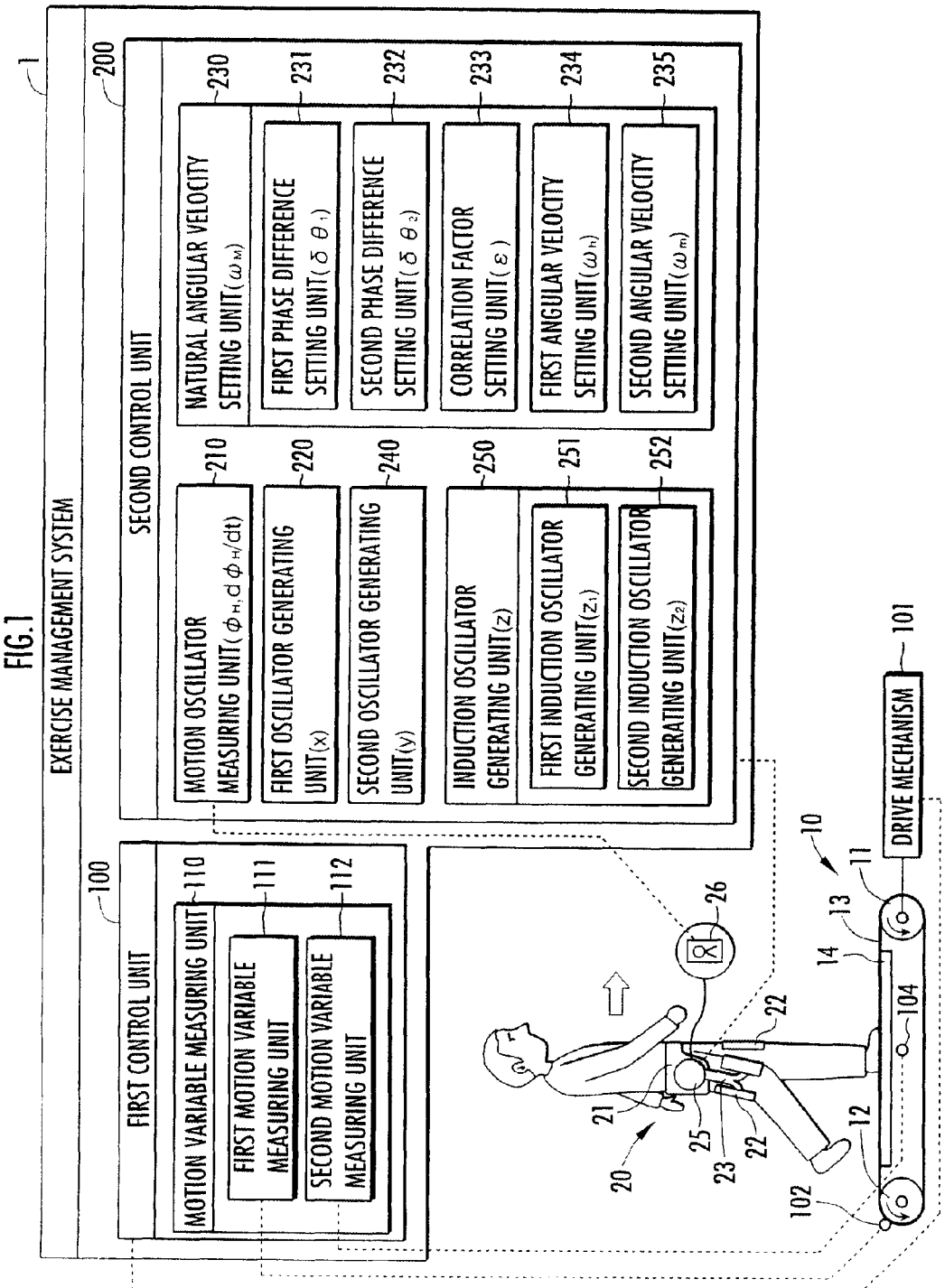
FIG. 1 is an illustrative configuration diagram of an exercise management system of the present invention.

An exercise management system 1 shown in FIG. 1 is for training a user (human being (animal)) by causing the user to walk (or run) with an appropriate scale and rhythm, while realizing harmonization between the motion of the user, the operation of a treadmill (first motion induction device) 10, and the operation of a walking motion induction device (second motion induction device) 20.

The treadmill 10 includes a driving roller 11 having a width slightly wider than the typical width of the human being, a driven roller 12 having an approximately same width as the driving roller 11, an endless belt (rotating body) 13 looped over the driving roller 11 and the driven roller 12, and a footplate 14 which supports from below the portion of the endless belt 13 on which the user stands. The driving roller 11 is driven by a drive mechanism 101 composed of a motor, transmission and the like. As the driving roller 11 is driven in the anticlockwise direction in the figure, the belt 13 rotates in the anticlockwise direction with the driven roller 12 driven in the same direction. This induces the user on the belt 13 to walk (or run) to the right in the figure. Further provided are a speed sensor 102 which outputs a signal responsive to the moving speed of the belt 13, and a pressure sensor 104 which outputs a signal responsive to the pressure received by the footplate 14. The treadmill 10 may be of any known configuration, including a commercially available one.

The walking motion induction device 20 includes a waist orthosis 21, thigh orthoses 22, force transmitting members 23, a battery 24, actuators (electric motors) 25, and hip joint angle sensors 26.

The waist orthosis 21 is made of combined rigid and flexible materials, and is attached to a user's waist. The thigh orthosis 22 is also made of combined rigid and flexible materials, and is attached to each of the front and back of a user's thigh. The force transmitting member 23, which is made of lightweight rigid plastic or any other material having a good shape retention property, extends downward from each side of the user's waist along the user's corresponding thigh and then bifurcates toward the front and back of the thigh. It is connected to the actuator 25 and the respective thigh orthoses 22. The battery 24 is housed in the waist orthosis 21 (for example, fixed between a plurality of materials constituting the waist orthosis 21) and supplies electric power to the actuator 25 and the like. The actuator 25 is mounted on the waist orthosis 21 and applies a force to the user's thigh via the force transmitting member 23 and the thigh orthosis 22. The hip joint angle sensor 26 is composed of a rotary encoder and the like provided on each of the sides of the user's waist, and outputs a signal responsive to a hip joint angle.

The exercise management system 1 includes a first control unit 100 and a second control unit 200.

The first control unit 100 is composed of a computer such as a microcomputer attached to the treadmill 10, and controls the speed of the driving roller 11 driven by the drive mechanism 102 and the like. The first control unit 100 includes a motion variable measuring unit 110. The motion variable measuring unit 110 is composed of a computer (containing CPU, ROM, RAM, I/O (input/output device) and others) serving as hardware and a part of the "exercise management program" of the present invention serving as software for providing functions to the computer. The motion variable measuring unit 110 includes a first motion variable measuring unit 111 and a second motion variable measuring unit 112.

The first motion variable measuring unit 111 measures the user's walking speed v as a first motion variable, based on an output of the speed sensor 102. The walking speed v increases as the user's walking motion scale increases or the walking motion rhythm becomes faster, and thus, the first motion variable corresponds to the motion variable representing both the motion scale and the motion rhythm of the user.

The second motion variable measuring unit 112 measures the user's walking rate (the number of steps per unit time) p as a second motion variable, based on an output of the pressure sensor 104. The walking rate p increases as the user's walking rhythm becomes faster, and thus, the second motion variable corresponds to the motion variable representing the motion rhythm of the user.

The second control unit (corresponding to the "control unit" of the present invention) 200 is composed of a computer housed in the waist orthosis 21 of the walking motion induction device 20 and the "exercise management program" of the present invention serving as the software providing the computer with the control function of the walking motion induction device 20 and the like.

The second control unit 200 includes a motion oscillator measuring unit 210, a first oscillator generating unit 220, a natural angular velocity setting unit 230, a second oscillator generating unit 240, and an induction oscillator generating unit 250.

The motion oscillator measuring unit 210 measures the user's hip joint angle $\phi_H$, based on an output of the hip joint angle sensor 26, as a "second motion oscillator" that periodically changes according to the walking motion. The hip joint angle $\phi_H$ increases in amplitude as the user's walking motion scale (represented by the step width or the like) increases, and thus, it corresponds to a "third motion oscillator" representing the user's motion scale. Further, the motion oscillator measuring unit 210 measures a hip joint angular velocity $d\phi_H/dt$ as a "first motion oscillator", based on an output of the hip joint angle sensor 26. The hip joint angular velocity $d\phi_H/dt$ increases in amplitude as the user's walking motion rhythm (represented by the waking rate or the like) becomes faster, and thus, it corresponds to a "fourth motion oscillator" representing the user's motion rhythm.

The first oscillator generating unit 220 generates a first oscillator x according to a first model, based on the hip joint angular velocity $d\phi_H/dt$ measured by the motion oscillator measuring unit 210 and a natural angular velocity $\omega_M$. The "first model" is a model for generating an output oscillation signal that changes over time at an angular velocity determined based on the natural angular velocity $\omega_M$, by mutual entrainment with the input oscillation signal.

The natural angular velocity setting unit 230 includes a first phase difference setting unit 231, a second phase difference setting unit 232, a correlation factor setting unit 233, a first angular velocity setting unit 234, and a second angular velocity setting unit 235.

The first phase difference setting unit 231 sets a phase difference between the angular velocity $\omega_H$ of the hip joint angular velocity $d\phi_H/dt$ and the oscillator x reflecting the natural angular velocity $\omega_M$ included in a van der Pol equation, as a first phase difference $\delta\theta_1$.

The second phase difference setting unit 232 sets, based on a "virtual model" representing the relationship between a virtual motion oscillator $\theta_h$ and a virtual induction oscillator (virtual induction oscillator) $\theta_m$, a phase difference between the virtual motion oscillator $\theta_h$ and the virtual induction oscillator $\theta_m$ as a second phase difference $\delta\theta_2$ $(=\theta_h-\theta_m)$.

The correlation factor setting unit 233 sets a correlation factor $\epsilon$ between the virtual motion oscillator $\theta_h$ and the virtual induction oscillator $\theta_m$ so that the second phase difference $\delta\theta_2$ set by the second phase difference setting unit 232 approaches the first phase difference $\delta\theta_1$ set by the first phase difference setting unit 231.

The first angular velocity setting unit 234 sets an angular velocity $\omega_h$ of the virtual motion oscillator $\theta_h$, based on the correlation factor $\epsilon$ set by the correlation factor setting unit 233.

The second angular velocity setting unit 235 sets an angular velocity $\omega_m$ of the virtual induction oscillator $\theta_m$, as a new natural angular velocity $\omega_M$, based on the angular velocity $\omega_h$ of the virtual motion oscillator $\theta_h$ set by the first angular velocity setting unit 234, so that the second phase difference $\delta\theta_2$ set by the second phase difference setting unit 232 approaches a target phase difference $\delta\theta_d$ set by a target phase difference setting unit 212.

The second oscillator generating unit 240 generates a second oscillator y, according to a second model, based on the hip joint angle $\phi_H$ measured by the motion oscillator measuring unit 210 and the natural angular velocity $\omega_M$ set by the natural angular velocity setting unit 230. The "second model" is a model for generating an output oscillation signal that changes over time at the angular velocity determined based on the natural angular velocity $\omega_M$, based on an input oscillation signal.

The induction oscillator generating unit 250 includes a first induction oscillator generating unit 251 and a second induction oscillator generating unit 252.

The first induction oscillator generating unit 251 generates a first induction oscillator $z_1$ based on the second oscillator y generated by the second oscillator generating unit 240 and the natural angular velocity $\omega_M$ set by the natural angular velocity setting unit 230. The first induction oscillator $z_1$ represents an elastic force of an elastic element, such as a virtual spring, that causes the hip joint angle $\phi_H$ measured by the motion oscillator measuring unit 210 to approach its target value $\phi_0$. The second induction oscillator generating unit 252 generates a second induction oscillator $z_2$ based on the second oscillator y generated by the second oscillator generating unit 240 and the natural angular velocity $\omega_M$ set by the natural angular velocity setting unit 230. It represents a damping force of a damping element, such as a virtual damper, that suppresses an increase in absolute value of the hip joint angle $\phi_H$ according to the hip joint angular velocity $d\phi_H/dt$ measured by the motion oscillator measuring unit 210. Then, the induction oscillator generating unit 250 generates an induction oscillator z, based on the first induction oscillator $z_1$ and the second induction oscillator $z_2$, as an instruction signal of the torque T around the hip joint which is to be applied to the user by the walking motion induction device 20.

The first control unit 100 and the second control unit 200 are communicable in a wireless manner. It is noted that the plurality of processing units 111, 112, 210, 220, . . . constituting the exercise management system may be arranged in any arbitrary pattern in the first control unit 100 and the second control unit 200; for example, a target walking ratio setting unit 130 may be provided in the second control unit 200 instead of the first control unit 100. Further, the first control unit 100 and the second control unit 200 may be configured with a same computer. The first control unit 100 and the second control unit 200 may also communicate with each other via a cable.

The functions of the exercise management system 1 having the above-described configuration will now be described with reference to FIGS. 2 to 4.

Figure 2:
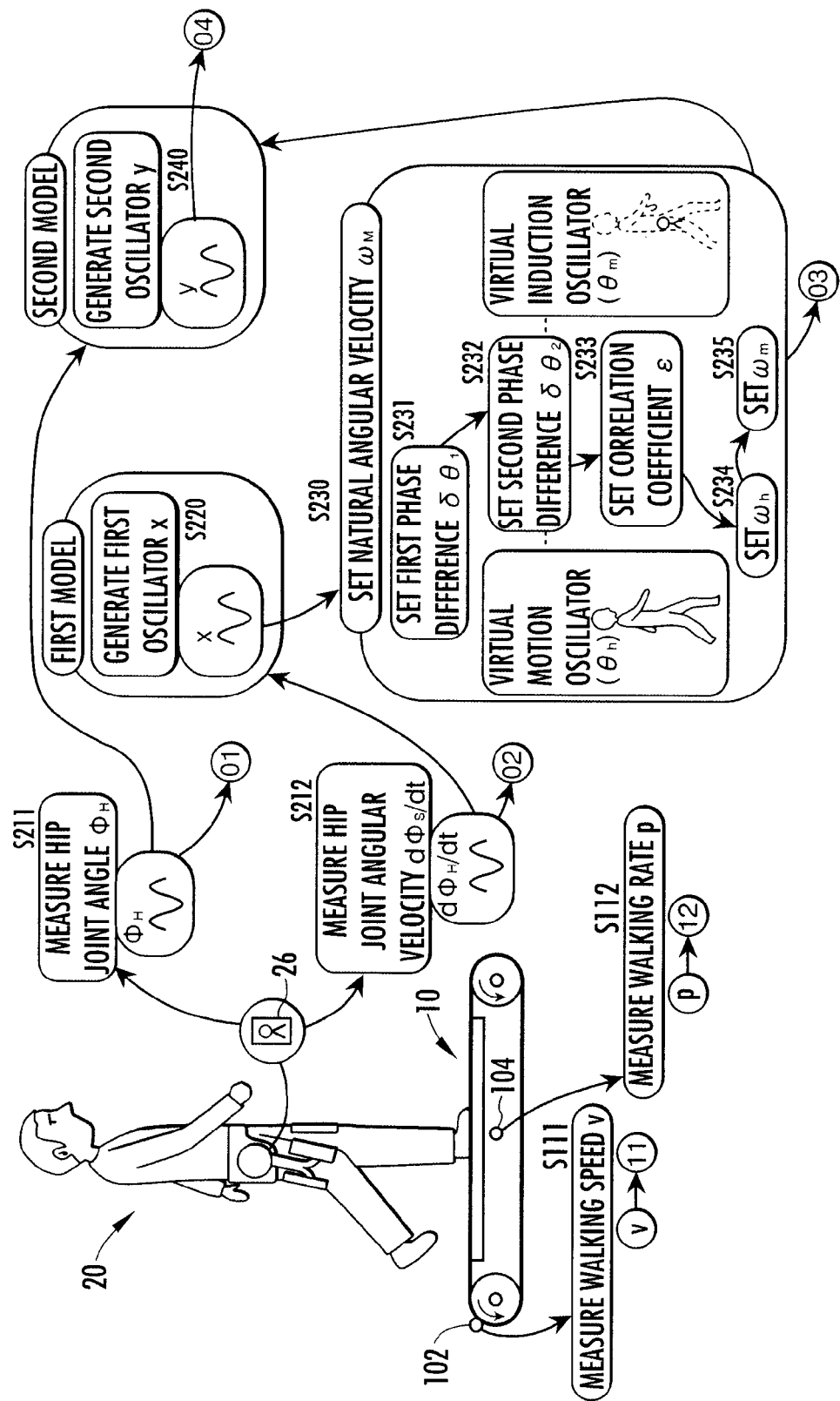
FIG. 2 is an explanatory diagram regarding an exercise management method of the present invention.

The first motion variable measuring unit 111 measures the user's walking speed v, based on an output of the speed sensor 102 corresponding to the speed of the belt 13 of the treadmill 10 (S111 in FIG. 2). The second motion variable measuring unit 112 measures the user's walking rate (the number of steps per unit time) p, based on the number of times the output of the pressure sensor 104, corresponding to the pressure applied to the footplate 14 of the treadmill 10, attains the peak per unit time (S112 in FIG. 2). It is noted that the walking rate p may be measured based on the change over time of the torque T around the hip joint which is applied to the user by the walking motion induction device 20. Further, an acceleration sensor may be attached to the user's body, in which case the walking rate p may be measured based on an output of the acceleration sensor corresponding to the acceleration in the vertical direction of the user.

The walking speed v measured by the first motion variable measuring unit 111 and the walking rate p measured by the second motion variable measuring unit 112 are transmitted from the first control unit 100 to the second control unit 200 in a wireless manner, and saved (or stored) in the RAM or the like of the second control unit 200.

The motion oscillator measuring unit 210 measures the user's left and right hip joint angles $\phi_H=(\phi_{HL}, \phi_{HR})$, based on the outputs of the hip joint angle sensors 26 (s211 in FIG. 2). Further, the motion oscillator measuring unit 210 measures the user's left and right hip joint angular velocities $d\phi_H/dt=(d\phi_{HL}/dt, d\phi_{HR}/dt)$, based on the outputs of the hip joint angle sensors 26 (s212 in FIG. 2).

The first oscillator generating unit 220 generates a first oscillator $x=(x_L, x_R)$ according to the "first model", based on the hip joint angular velocity $d\phi_H/dt$ measured by the motion oscillator measuring unit 210 and the latest natural angular velocity $\omega_M=(\omega_{ML}, \omega_{MR})$ stored in the memory (s220 in FIG. 2). The first model is a model which represents the correlation of a plurality of first elements, such as virtual left and right legs, whose outputs change in accordance with the first motion oscillator such as the hip joint angular velocity $d\phi_H/dt$. Specifically, the "first model" is a model for generating an output oscillation signal (i.e., output oscillation signal of each of the first elements) that changes over time at an angular velocity determined based on the natural angular velocity, by mutual entrainment with an input oscillation signal. The first model is expressed, e.g., using the van der Pol equations represented by the following expressions (1). The first oscillator generating unit 220 inputs the hip joint angular velocity $d\phi_H/dt$ (first motion oscillator) to the first model as the input oscillation signal, to generate the first oscillator $x=(x_L, x_R)$ as the output oscillation signal.

$$(d^2 x_L / dt^2) = \xi(1 - x_L^2)(dx_L/dt) - \omega_{ML}^2 x_L + g(x_L - x_R) + K(d\phi_{HL}/dt), \quad (1)$$

$$(d^2 x_R / dt^2) = \xi(1 - x_R^2)(dx_R/dt) - \omega_{MR}^2 x_R + g(x_R - x_L) + K(d\phi_{HR}/dt)$$

where "$\xi$" is a coefficient (>0) that is set so that the first oscillator x and its one-time temporal differentiation (dx/dt) draw stable limit cycles on the x–(dx/dt) plane. "g" is a first correlation factor representing the correlation of the virtual left and right legs (first elements) in the first model. "K" is a feedback coefficient. It is noted that the natural angular velocity $\omega_M$ may be set arbitrarily within the range not largely deviating from the actual walking assist rhythm (walking induction rhythm) by the walking motion induction device 20.

The first oscillator $x=(x_L, x_R)$ is calculated or generated according to the Runge-Kutta method. The components $x_L$ and $x_R$ of the first oscillator x represent the virtual walking assist rhythms for the left and right legs, respectively. The oscillator x tends to periodically change or oscillate at an autonomous rhythm reflecting the "natural angular velocity" $\omega_M$, while being harmonized with the rhythm of the hip joint angular velocity $d\phi_H/dt$ that charges over time at the rhythm (angular velocity) approximately the same as that of the actual walking motion, by virtue of the "mutual entrainment" which is a property of the van der Pol equation.

It is noted that the first oscillator x may be generated based on any kind of oscillator that oscillates in a rhythm reflecting the user's walking motion rhythm (motion rhythm), such as a hip joint angle $\phi_H$, angle or angular velocity of knee joint, ankle joint, shoulder joint, elbow joint or the like, the walker's landing sound, respiratory sound, intermittently generated voice sound, or the like, instead of or in addition to the hip joint angular velocity $d\phi_H/dt$.

Further, the first model may be expressed by a van der Pol equation in the form different from that of the van der Pol equation represented by the expression (1). The first model may be expressed by any kind of equation that can generate an oscillator with the effect of mutual entrainment with the motion oscillator such as the hip joint angular velocity $d\phi_H/dt$.

As described above, the first oscillator x is generated as an output of the first element, according to the first model which represents the relationship of the plurality of first elements (left and right legs) whose outputs change in accordance with the motion oscillator such as the hip joint angular velocity $d\phi_H/dt$ (expression (1), s220 in FIG. 2). Accordingly, an appropriate first oscillator x can be generated in consideration of the relationship between the plurality of first elements, by allowing the relationship between the plurality of first elements concerning the user's actual motion to be reflected to the first correlation factor g or the like in the first model. For example, in the case where the left and right legs, or a plurality of joints of the same leg, are assumed as the plurality of first elements, the first oscillator x is generated so as to reflect the qualitative relationship between the left and right legs such as their alternate backward and forward movements, or the qualitative relationship between the joints of the same leg such as the period or phase difference between the leg motion around the hip joint and the leg motion around the knee joint. This allows the rhythm and scale of the induction oscillator inducing the user's motion to be set as appropriate in consideration of the relationship concerned.

Subsequently, the natural angular velocity setting unit 230 newly sets a natural angular velocity $\omega_M$ according to a virtual model including two virtual oscillators, based on the target phase difference $\delta\theta_d$ stored in the memory and the first oscillator x generated by the first oscillator generating unit 220 (s230 in FIG. 2).

Specifically, the first phase difference setting unit 231 firstly sets, for each of the left and right components, a phase difference $\theta_H - \theta_M$ between the phase $\theta_H$ of the hip joint angular velocity (first motion oscillator) $d\phi_H/dt$ measured by the motion oscillator measuring unit 210 and the phase $\theta_M$ of the first oscillator x generated by the first oscillator generating unit 220, as a first phase difference $\delta\theta_1$ (s231 in FIG. 2).

Next, on the condition that the first phase difference $\delta\theta_1$ set by the first phase difference setting unit 231 remained constant over the past three walking periods, the second phase difference setting unit 232 sets the phase difference $\theta_h - \theta_m$ between the virtual motion oscillator $\theta_h$ and the virtual induction oscillator $\theta_m$ represented by the following expression (2.3) as a second phase difference $\delta\theta_2$, for each of the left and right components, according to the "virtual model" represented by the following expressions (2.1) and (2.2) (s232 in FIG. 2).

$$d\theta_h/dt = \omega_h + \epsilon \cdot \sin(\theta_{mL} - \theta_{hL}) \quad (2.1)$$

$$d\theta_m/dt = \omega_m + \epsilon \cdot \sin(\theta_{hL} - \theta_{mL}) \quad (2.2)$$

$$\delta\theta_2 = \arcsin[(\omega_h - \omega_m)/2\epsilon] \quad (2.3)$$

where $\epsilon = (\epsilon_L, \epsilon_R)$ is a correlation factor between the virtual motion oscillator $\theta_h = (\theta_{hL}, \theta_{hR})$ and the virtual induction oscillator $\theta_m = (\theta_{mL}, \theta_{mR})$ in the virtual model for each of the left and right components. Further, $\omega_h$ is an angular velocity of the virtual motion oscillator $\theta_h$, and $\omega_m$ is an angular velocity of the virtual induction oscillator $\theta_m$.

Subsequently, the correlation factor setting unit 233 sets a correlation factor $\epsilon$ such that the difference $\delta\theta_1 - \delta\theta_2$ between the first phase difference $\delta\theta_1$ set by the first phase difference setting unit 231 and the second phase difference $\delta\theta_2$ set by the second phase difference setting unit 232 becomes minimal (s233 in FIG. 2).

Specifically, the correlation factor $\epsilon$ in a discrete time $t_{id}$ (d=1, 2, ...) where the hip joint angular velocity (motion oscillator) $d\phi_H/dt$ becomes 0 is sequentially set for each of the left and right components, according to the following expression (2.4).

$$\epsilon(t_{id+1}) = \epsilon(t_{id}) - \eta\{V_1(t_{id+1}) - V_1(t_{id})\}/\{\epsilon(t_{id}) - \epsilon(t_{id-1})\},$$

$$V_1(t_{id+1}) \equiv (1/2)\{\delta\theta_1(t_{id+1}) - \delta\theta_2(t_{id})\}^2 \quad (2.4)$$

where each component of $\eta = (\eta_L, \eta_R)$ is a coefficient which represents stability of the potential $V = (V_L, V_R)$ that causes each of the left and right components of the first phase difference $\delta\theta_1$ to approach the corresponding component of the second phase difference $\delta\theta_2$.

Next, on the condition that the angular velocity $\omega_m$ of the virtual induction oscillator $\theta_m$ is constant, the first angular velocity setting unit 234 sets the angular velocity $\omega_h$ of the virtual motion oscillator $\theta_h$ according to the following expression (2.5), for each of the left and right components, based on the correlation factor $\epsilon$ set by the correlation factor setting unit 233, so that each component of the difference $\delta\theta_1 - \delta\theta_2$ between the first and second phase differences becomes minimal (s234 in FIG. 2).

$$\omega_h(t_{id}) = -\alpha \int dt \left[4\epsilon(t_{id})^2 - \{\omega_h(t) - \omega_m(t_{id})\}^2\right]^{1/2} \times \quad (2.5)$$
$$\sin[\sin^{-1}\{(\omega_h(t) - \omega_m(t_{id-1}))/2\epsilon(t_{id})\} - \delta\theta_1(t_{id})]$$

where each component of $\alpha = (\alpha_L, \alpha_R)$ is a coefficient which represents stability of the system.

Subsequently, the second angular velocity setting unit 235 sets the angular velocity $\omega_m$ of the virtual induction oscillator $\theta_m$ as a new natural angular velocity $\omega_M$, for each of the left and right components, based on the angular velocity $\omega_h$ of the virtual motion oscillator $\theta_h$ set by the first angular velocity setting unit 234 (s235 in FIG. 2). Specifically, the second angular velocity setting unit 235 sets the angular velocity $\omega_m = (\omega_{mL}, \omega_{mR})$ of the virtual induction oscillator $\theta_m$ according to the following expression (2.6), for each of the left and right components, so that the second phase difference $\delta\theta_2$ approaches the target phase difference $\delta\theta_d$.

$$\omega_m(t_{id}) = \beta \int dt \cdot ([4\epsilon(t_{id})^2 - \{\omega_h(t_{id}) - \omega_m(t)\}^2) \times \quad (2.6)$$
$$\sin[\sin^{-1}\{(\omega_h(t_{id}) - \omega_m(t))/2\epsilon(t_{id})\} - \delta\theta_d])$$

where each component of $\beta = (\beta_L, \beta_R)$ is a coefficient representing stability of the system.

Subsequently, the second oscillator generating unit 240 generates a second oscillator $y = (y_{L+}, y_{L-}, y_{R+}, y_{R-})$ according to a "second model", based on the hip joint angle $\phi_H$ measured by the motion oscillator measuring unit 210 and the new natural angular velocity $\omega_M$ set by the natural angular velocity setting unit 230 (s240 in FIG. 2). The second model is a model which represents correlation between a plurality of second elements, such as a plurality of neural elements, whose outputs change in accordance with the motion oscillator such as the hip joint angle $\phi_H$. More specifically, the second model is expressed by the following simultaneous differential equations (3), which include: a motion variable $u_i$ (i=L+, L−, R+, R−) corresponding to changes in membrane potential of neural elements L+ and L− which govern the motions of the left thigh in the bending direction (forward) and the stretching direction (backward), respectively, and neural elements R+ and R− which govern the motions of the right thigh in the bending direction and the stretching direction, respectively; and a self-control factor $v_i$ reflecting an adaptive effect of the neural element i.

$$\tau_{1L+} \cdot du_{L+}/dt = -u_{L+} + w_{L+/L-} y_{L-} + w_{L+/R+} y_{R+} - \lambda_L v_{L+} + f_1(\omega_{ML}) + f_2(\omega_{ML}) K(\phi_L),$$

$$\tau_{1L-} \cdot du_{L-}/dt = -u_{L-} + w_{L-/L+} y_{L+} + w_{L-/R-} y_{R-} - \lambda_L v_{L-} + f_1(\omega_{ML}) + f_2(\omega_{ML}) K(\phi_L),$$

$$\tau_{1R+} \cdot du_{L+}/dt = -u_{L+} + w_{R+/L+} y_{L+} + w_{R+/R-} y_{R-} - \lambda_R v_{R+} + f_1(\omega_{MR}) + f_2(\omega_{MR}) K(\phi_R),$$

$$\tau_{1R-} \cdot du_{R-}/dt = -u_{R-} + w_{R-/L+} y_{L-} + w_{R-/R+} y_{R+} - \lambda_R v_{R-} + f_1(\omega_{MR}) + f_2(\omega_{MR}) K(\phi_R),$$

$$\tau_{2i} \cdot dv_i/dt = -v_i + y_i,$$

$$y_i = H(u_i - u_{th}), H \equiv 0 (u_i < u_{th}), 1 (u_i \geq u_{th}) \text{ or}$$

$$y_i = f_s(u_i) \equiv 1/\{1 + \exp(-u_i/\xi)\} \quad (3)$$

where $\tau_{1i}$ is a time constant which defines change characteristics of the state variable $u_i$ and it has a dependence on the new natural angular velocity $\omega_M$ as expressed by the following expression (3.1) for each of the left and right components.

$$\tau_{1i} = t(\omega_{ML})/\omega_{ML} - \gamma_L \quad (i = L+, L-)$$

$$t(\omega_{MR})/\omega_{MR} - \gamma_R \quad (i = R+, R-) \quad (3.1)$$

where $t(\omega)$ is a coefficient having a dependence on $\omega$. $\gamma = (\gamma_L, \gamma_R)$ is a constant. $\tau_{2i}$ is a time constant which defines change characteristics of the self-control factor $v_i$. $w_{i/j}$ (<0) is a second correlation factor (constant) representing the relationship between a plurality of second elements (neural elements) i and j. $\lambda_L$ and $\lambda_R$ are habituation coefficients. K is a feedback coefficient in accordance with the hip joint angle $\phi_H$.

$f_1$ and $f_2$ are functions defined by the following expressions (3.2) and (3.3), respectively.

$$f_1(\omega) \equiv c \cdot \omega \quad (c > 0) \quad (3.2)$$

$$f_2(\omega) \equiv c_0 + c_1 \omega + c_2 \omega^2 \quad (3.3)$$

The coefficients c, $c_0$, $c_1$, $c_2$ of $f_1(\omega_M)$ and $f_2(\omega_M)$, the functions of the new natural angular velocity $\omega_M$, may be set as coefficients corresponding to a target motion rhythm set by a target motion setting unit 211.

It is noted that the second oscillator $y_i$ may be generated based on any kind of oscillator that oscillates in a rhythm linked to the walking motion rhythm, such as a hip joint angular velocity $d\phi_H/dt$, angle or angular velocity of knee joint, ankle joint, shoulder joint, elbow joint or the like, the walker's landing sound, respiratory sound, intermittently generated voice sound, or the like, instead of or in addition to the hip joint angle $\phi_H$.

When the value of the motion variable $u_i$ is less than a threshold value $u_{th}$, the second oscillator $y_i$ is 0; whereas when the value of the motion variable $u_i$ is not less than the threshold value $u_{th}$, the second oscillator $y_i$ takes the value of $u_i$. Alternatively, the second oscillator $y_i$ is defined by a sigmoid function fs (see the expression (3)). Thus, for the motions of the thighs in the bending direction (forward), the second oscillators $y_{L+}$ and $y_{R+}$ corresponding to the outputs of the second elements (neural elements) L+ and R+, respectively, which govern those motions become greater than the outputs of the other second elements. Further, for the motions of the thighs in the stretching direction (backward), the second oscillators $y_{L-}$ and $y_{R-}$ corresponding to the outputs of the second elements L− and R−, respectively, which govern those motions become greater than the outputs of the other second elements. The frontward or backward motion of the leg (thigh) is identified, e.g., by the polarity of the hip joint angular velocity $d\phi_H/dt$.

As described above, the second oscillator $y_i$ is generated as the output of the second element i, according to the second model which expresses the relationship between a plurality of second elements whose outputs charge according to the motion oscillator such as the hip joint angular velocity $d\phi_H/dt$ (the expression (3), s240 in FIG. 2). Thus, by causing the correlation between the plurality of second elements concerning the user's actual motion to be reflected to the second correlation factor $w_{i/j}$ in the second model, an appropriate second oscillator $y_i$ may be generated in consideration of the correlation between those second elements. For example, in the case where the user's neural elements (neural group or neuron group) are assumed to be the second elements, the second oscillator $y_i$ is generated in the form reflecting the qualitative relationship between the neural elements governing the walking by the left and right legs or the like. This enables the rhythm and scale of the induction oscillator inducing the user's motion to be set as appropriate in consideration of the relationship concerned.

Figure 3:
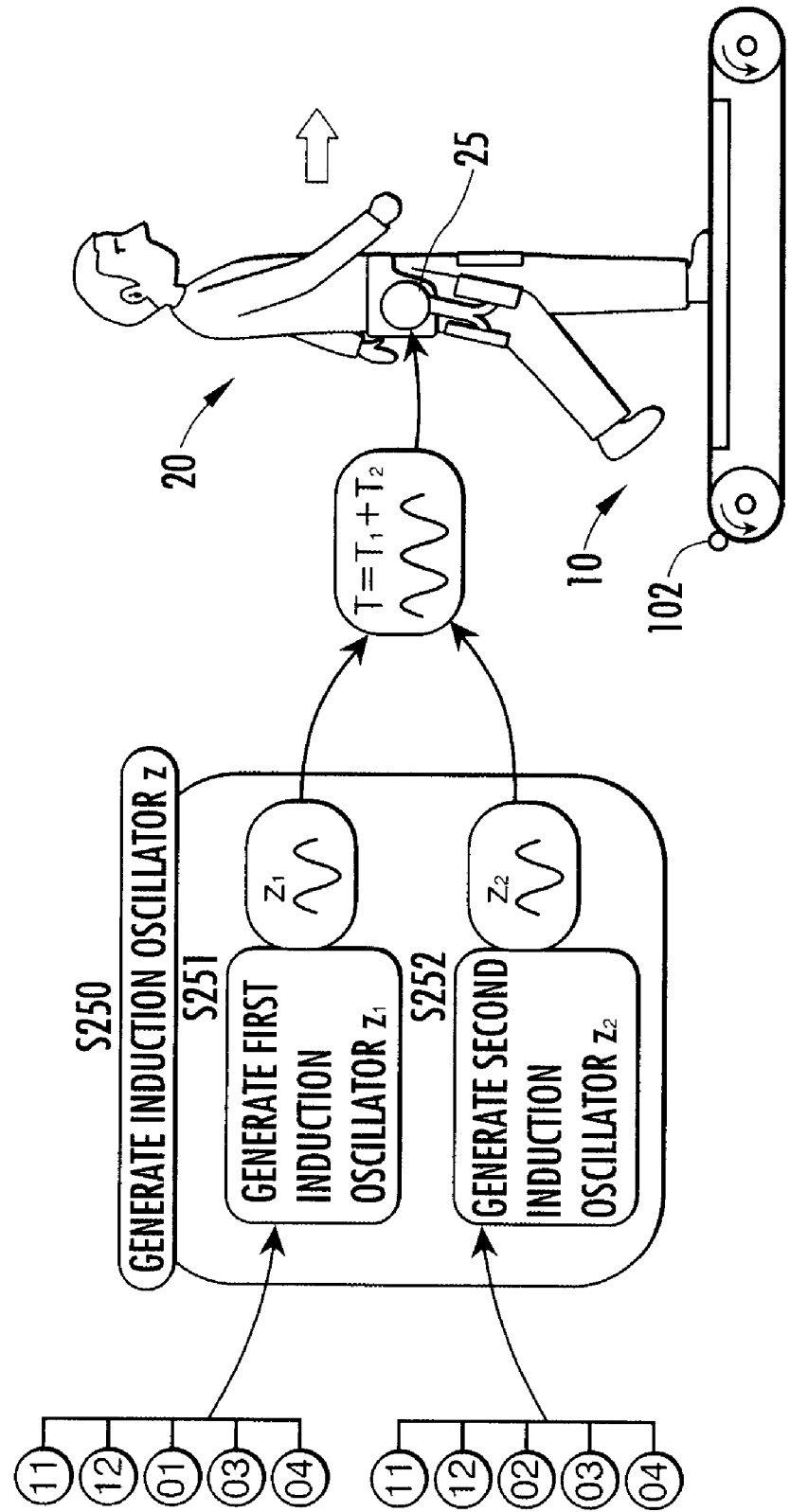
FIG. 3 is another explanatory diagram regarding the exercise management method of the present invention.

Next, the induction oscillator generating unit 250 generates the induction oscillator z, based on the walking speed v measured by the first motion variable measuring unit 111, the walking rate p measured by the second motion variable measuring unit 112, the hip joint angle (third motion oscillator) $\phi_H$ measured by the motion oscillator measuring unit 210, the hip joint angular velocity (fourth motion oscillator) $d\phi_H/dt$ measured by the motion oscillator measuring unit 210, the second oscillator $y_i$, generated by the second oscillator generating unit 240, and the new natural angular velocity $\omega_M$ set by the natural angular velocity setting unit 230 (s250 in FIG. 3).

Specifically, a first induction oscillator $z_1$ is generated according to the following expression (4) (s251 in FIG. 3).

$$z_{1L} = g_1 + (p_0, \omega_{mL}) g_+ (q_0, \phi_{HL}) y_{L+} - g_1 - (p_0, \omega_{mL}) g_- (q_0, \phi_{HL}) y_{L-},$$

$$z_{1R} = g_1 + (p_0, \omega_{mL}) g_+ (q_0, \phi_{HR}) y_{R+} - g_1 - (p_0, \omega_{mR}) g_- (q_0, \phi_{HR}) y_{R-},$$

$$p_0 = (v/k_0)^{1/2}, q_0 = (vk_0)^{1/2} \quad (4)$$

where "$g_{1+}$", "$g_{1-}$" "$g_+$", and "$g_-$" are functions defined by the following expressions (4.1) to (4.4), respectively.

$$g_{1+}(p_0, \omega) = \Sigma_k a_{k+}(p_0) \omega^k \quad (a_{k+}(p_0): \text{coefficient}, k=0 \text{ to } 3) \quad (4.1)$$

$$g_{1-}(p_0, \omega) = \Sigma_k a_{k-}(p_0) \omega^k \quad (a_{k-}(p_0): \text{coefficient}, k=0 \text{ to } 3) \quad (4.2)$$

$$g_+(q_0, \phi) \equiv c_{1+}(\phi - \phi_{0+}(q_0)) + c_{2+}(\phi - \phi_{0+}(q_0))^3$$

($c_{1+}, c_{2+}$: coefficients; $\phi_{0+}$: target value of hip joint angle $\phi_H$ in bending direction) (4.3)

$$g_-(q_0, \phi) \equiv c_{1-}(\phi - \phi_{0-}(q_0)) + c_{2-}(\phi - \phi_{0-}(q_0))^3$$

($c_{1-}, c_{2-}$: coefficients; $\phi_{0-}$: target value of hip joint angle $\phi_H$ in stretching direction) (4.4)

The target angles $\phi_{0+}(q_0)$ and $\phi_{0-}(q_0)$ of the hip joint angle $\phi_H$ are functions of a recommended step width $q_0$ ($=(vk_0)^{1/2}$) which corresponds to the target walking ratio $k_0$ and walking speed v, and may be corrected based on the deviation $\delta q$ of the user's step width q ($=v/p$) from the recommended step width $q_0$. Further, the coefficients $a_{k+}(p_0)$ and $a_{k-}(p_0)$ included in the first coefficients $g_{1+}(p_0, \omega_M)$ and $g_{1-}(p_0, \omega_M)$ are functions of a recommended walking rate $p_0$ ($=(v/k_0)^{1/2}$) which corresponds to the target walking ratio $k_0$ and walking speed v, and may be corrected based on the deviation $\delta p$ of the user's walking rate p (=v/q) from the recommended walking rate $p_0$.

Figure 4:
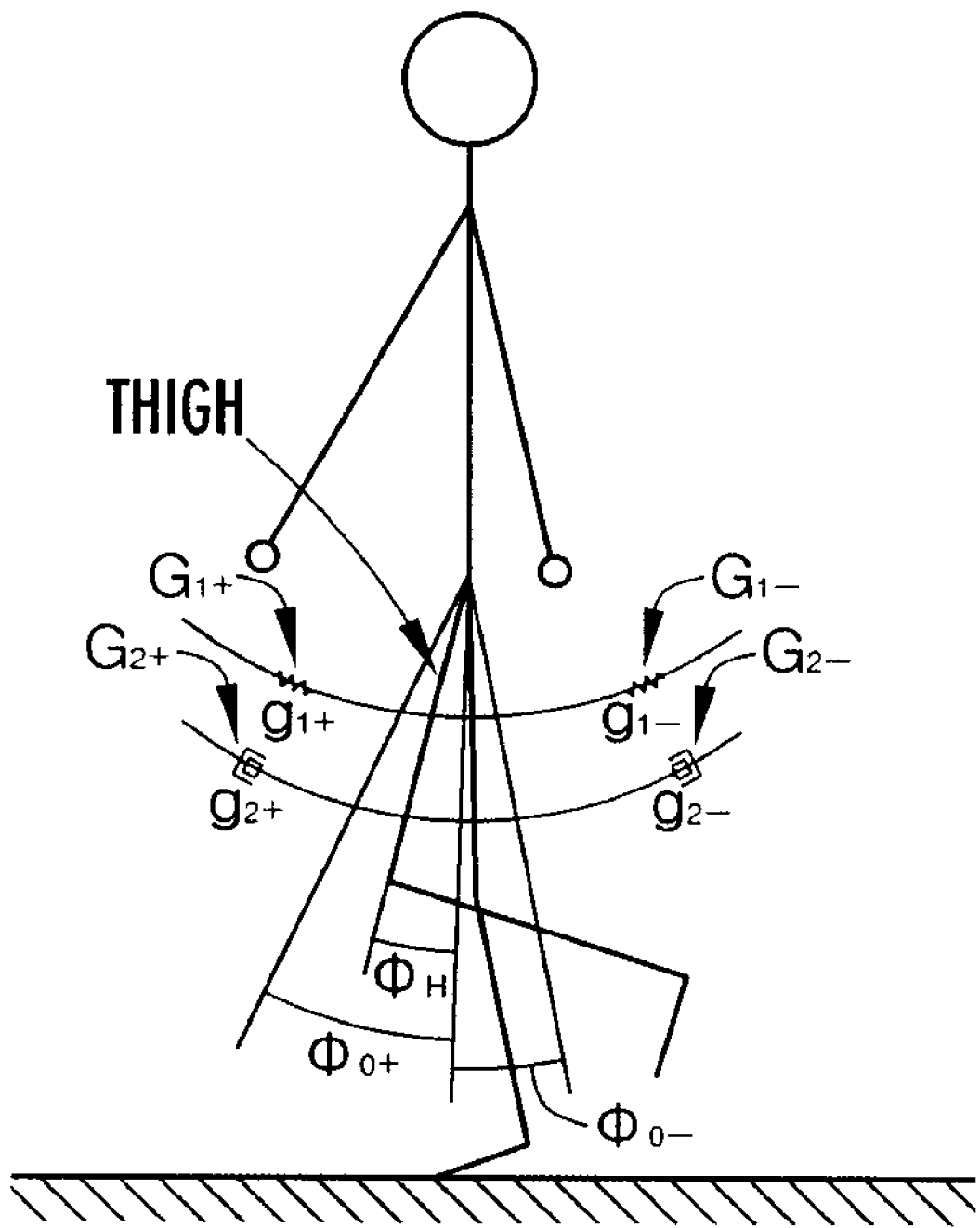
FIG. 4 is an explanatory diagram of virtual springs and dampers inducing walking motion.

The first induction oscillator $z_1$ represents elastic forces of two virtual springs $G_{1+}$ and $G_{1-}$, as shown in FIG. 4, which have the first coefficients $g_{1+}$ and $g_{1-}$, respectively, as their spring coefficients (elastic coefficients). The first coefficients $g_{1+}$ and $g_{1-}$ represent the gradients of a first potential (a potential of an elastic element such as a virtual spring) which cause the hip joint angle (the third motion oscillator) $\phi_H$ to approach the target angles $\phi_{0+}$ (>0) and $\phi_{0-}$ (<0) in accordance with the target motion scale, according to the walking speed (first motion variable) v and the natural angular velocity $\omega_M$ (see the expressions (4.1) and (4.2)). That is, the first induction oscillator $z_1$ represents elastic forces of the virtual elastic elements which have the first coefficients $g_{1+}$, $g_{1-}$ as the elastic coefficients (spring coefficients) and which restore the value of the hip joint angle $\phi_H$ to the target angles $\phi_{0+}$ and $\phi_{0-}$. This enables the user's motion to be induced by the first induction oscillator $z_1$ so that the hip joint angle $\phi_H$ matches the target angle $\phi_{0+}$, $\phi_{0-}$ according to the target walking ratio $k_0$ and walking speed v, and to be induced with the rhythm and scale reflecting the elastic elements of the user's body such as the elastic force generated during the transition from the muscle contraction state to the muscle stretch state.

The elastic force of the virtual spring $G_{1+}$ represents the force that acts on the user's thigh to bring the hip joint angle $\phi_H$ close to its target value $\phi_{0+}$ according to the spring coefficient $g_{1+}$ (see the expression (4)). Specifically, when the hip joint angle $\phi_H$ is less than the target angle $\phi_{0+}$, the elastic force of the spring $G_{1+}$ acts on the thigh in such a way as to move the thigh in the direction of increasing the hip joint angle $\phi_H$ (forward). When the hip joint angle $\phi_H$ exceeds the target angle $\phi_{0+}$, the elastic force of the spring $G_{1+}$ acts on the thigh in such a way as to move the thigh in the direction of decreasing the hip joint angle $\phi_H$ (backward).

Further, the elastic force of the other virtual spring $G_{1-}$ represents the force that acts on the user's thigh to bring the hip joint angle $\phi_H$ close to the target angle $\phi_{0-}$ according to the spring coefficient $g_{1-}$ (see the expression (4)). Specifically, when the hip joint angle $\phi_H$ exceeds the target angle $\phi_{0-}$, the elastic force of the spring $G_{1-}$ represents the force that acts on the thigh in such a way as to move the thigh in the direction of decreasing the hip joint angle $\phi_H$ (backward). When the hip joint angle $\phi_H$ is less than the target angle $\phi_{0-}$, the elastic force of the spring $G_{1-}$ represents the force that acts on the thigh in such a way as to move the thigh in the direction of increasing the hip joint angle $\phi_H$ (forward).

Further, as described above, there are uneven outputs from some of the plurality of second elements i (=L+, L−, R+, R−) in accordance with the forward or backward movement of the thighs, which prevents the elastic forces of the two virtual springs $G_{1+}$ and $G_{1-}$ from being cancelled out.

Specifically, in the case where the left thigh is moving forward, the value of the second oscillator $y_{L+}$ as the output of the second element L+, which is one of the elements governing this motion, becomes greater than the value of the second oscillator $y_{L-}$ as the output of the other second element L−. Accordingly, the first induction oscillator $z_{1L}$ represented by the expression (4) is approximated by the following expression (4a).

$$z_{1L} \approx g_{1+}(\omega_{mL})g_+(\phi_{HL})y_{L+} \quad (4a)$$

Therefore, in the case where the left thigh is moving forward, of the elastic forces of the two virtual springs $G_{1+}$ and $G_{1-}$, the elastic force of the spring $G_{1+}$ acting on the user's thigh in such a way as to bring the hip joint angle $\phi_H$ close to the target angle $\phi_{0+}$ for the front side is reflected predominantly. This avoids cancellation of the elastic forces of the two virtual springs $G_{1+}$ and $G_{1-}$ with each other.

Further, in the case where the left thigh is moving backward, the value of the second oscillator $y_{L-}$ as the output of the second element L−, which is one of the elements governing this motion becomes greater than the value of the second oscillator $y_{L+}$ as the output of the other second element L+. Accordingly, the first induction oscillator $z_{1L}$ represented by the expression (4) is approximated by the following expression (4b).

$$z_{1L} \approx -g_{1-}(\omega_{mL})g_-(\phi_{HL})y_{L-} \quad (4b)$$

Therefore, in the case where the left thigh is moving backward, of the elastic forces of the two virtual springs $G_{1+}$ and $G_{1-}$, the elastic force of the virtual spring $G_{1-}$ acting on the user's thigh in such a way as to bring the hip joint angle $\phi_H$ close to the target angle $\phi_{0-}$ for the back side is reflected predominantly. This avoids cancellation of the elastic forces of the two virtual springs $G_{1+}$ and $G_{1-}$ with each other. The same applies to the motion of the right leg (thigh).

It is noted that a sigmoid function fs (see the expression (3)) having the hip joint angular velocity $d\phi_H/dt$ as a variable may be incorporated into the first coefficients $g_{1+}$, $g_{1-}$, and a first torque $T_1$ may be generated in the form unevenly reflecting part of the second oscillators $y_i$ as the outputs of the plurality of second elements i, in accordance with the forward or backward movement of the thigh specified by the polarity of the hip joint angular velocity $d\phi_H/dt$. This again prevents the elastic forces of the two virtual springs $G_{1+}$ and $G_{1-}$ from being cancelled out.

Furthermore, a second induction oscillator $z_2$ is set according to the following expression (5) (s252 in FIG. 3).

$$z_{2L} = -g_{2+}(p_0, \omega_{mL})(d\phi_{HL}/dt)H_+(\phi_{HL})y_{L+} + g_{2-}(p_0, \omega_{mL})(d\phi_{HL}/dt)H_-(\phi_{HL})y_{L-},$$

$$z_{2R} = -g_{2+}(p_0, \omega_{mR})(d\phi_{HR}/dt)H_+(\phi_{HR})y_{R+} + g_{2-}(p_0, \omega_{mR})(d\phi_{HR}/dt)H_-(\phi_{HR})y_{R-} \quad (5)$$

where "$g_{2+}$", "$g_{2-}$", "$H_{30}$" and "$H_{31}$" are functions defined by the following expressions (5.1) to (5.4).

$$g_{2+}(p_0,\omega) = \Sigma_k b_{k+}(p_0)\omega^k$$

$$(b_{k+}(p_0)\text{:coefficient, k=0 to 3}) \quad (5.1)$$

$$g_{2-}(p_0,\omega) = \Sigma_k b_{k-}(p_0)\omega^k$$

$$(b_{k-}(p_0)\text{:coefficient, k=0 to 3}) \quad (5.2)$$

$$H_+(\phi) = 0(\phi \leq 0), 1(\phi > 0) \quad (5.3)$$

$$H_-(\phi) = 0(\phi > 0), 1(\phi \leq 0) \quad (5.4)$$

The coefficients $b_{k+}(p_0)$ and $b_{k-}(p_0)$ included in the second coefficients $g_{2+}(p_0, \omega_M)$ and $g_{2-}(p_0, \omega_M)$ are functions of a recommended walking rate $p_0$ (=$(v/k_0)^{1/2}$) which corresponds to the target walking ratio $k_0$ and walking speed v, and may be corrected based on the deviation $\delta p$ of the user's walking rate p (=v/q) from the recommended walking rate $p_0$.

The second induction oscillator $z_2$ represents damping forces of two virtual dampers $G_{2+}$ and $G_{2-}$, as shown in FIG. 4, which have the second coefficients $g_{2+}$ and $g_{2-}$, respectively, as damper coefficients (damping coefficients). The second coefficients $g_{2+}$ and $g_{2-}$ represent the gradients of a second potential (a potential of a virtual damper (damping element)) which suppress an increase in absolute value of the hip joint angle $\phi_H$ according to the natural angular velocity $\omega_M$ (see the expressions (5.1) and (5.2)). That is, the second induction oscillator $z_2$ represents damping forces of the virtual damping elements such as dampers which have the second coefficients $g_{2+}$, $g_{2-}$ as the damping coefficients (damper coefficients) and which suppress an increase in absolute value of the hip joint angle (third motion oscillator) $\phi_H$ according to the hip joint angular velocity (fourth motion oscillator $d\phi_H/dt$. This enables the user's motion to be induced by the second induction oscillator $z_2$ to suppress an increase in absolute value of the hip joint angle $\phi_H$ according to the hip joint angular velocity $d\phi_H/dt$, and to be induced with the rhythm and scale reflecting the damping elements of the user's body such as the viscous force generated during the transition from the muscle stretch state to the muscle flexed state.

The damping force of one virtual damper $G_{2+}$ represents the force that acts on the user's thigh to prevent an increase in absolute value of the hip joint angle $\phi_H$ toward the front side (bending side), according to the damper coefficient $g_{2+}$ and the hip joint angular velocity $d\phi_H/dt$ (see the expression (5)). In other words, the damping force of the virtual damper $G_{2+}$ represents the force that acts on the thigh in such a way as to prevent the excessive forward movement of the thigh.

Further, the elastic force of the other virtual damper $G_{2-}$ represents the force that acts on the user's thigh to prevent an increase in absolute value of the hip joint angle $\phi_H$ toward the back side (stretch side), according to the damper coefficient $g_{2-}$ and the hip joint angular velocity $d\phi_H/dt$ (see the expression (5)). In other words, the damping force of the virtual damper $G_{2-}$ represents the force that acts on the thigh in such a way as to prevent the excessive backward movement of the thigh.

Furthermore, the second induction oscillator $z_2$ includes step functions $H_+$ and $H_-$ as the functions of the hip joint angle $\phi_H$. This prevents the damping forces of the two virtual dampers $G_{2+}$ and $G_{2-}$ from being cancelled out.

Then, the currents $I(z)=(I_L(z_{1L}+z_{2L}), I_R(z_{1R}+z_{2R}))$ corresponding to the induction oscillator z $(=z_1+z_2)$ including the first induction oscillator $z_1=(z_{1L}, z_{1R})$ and the second induction oscillator $z_2=(z_{2L}, z_{2R})$ generated by the induction oscillator generating unit 250 are supplied from the battery 206 to the left and right actuators 210, respectively, thereby causing the forces (torques around the hip joints) T(I) corresponding to the supplied currents I to act on the user's thighs.

Thereafter, the above-described processing (s111, s112, s210, . . . , s240 in FIG. 2 and s250 in FIG. 3) is repeated to allow the user to walk, with the torque T around the hip joint applied to the user by the operation of the walking motion induction device 20.

According to the exercise management system 1 exerting the above-described functions, the user's walking or running motion is induced while the user's walking speed is being adjusted by the operation of the treadmill (first motion induction device) 10 and the motion scale is being adjusted with the rhythm harmonized with the user's walking rate by the operation of the walking motion induction device (second motion induction device) 20. At this time, the operation of the walking motion induction device 20 is controlled based on the walking speed (first motion variable) v and the walking rate (second motion variable) p of the user who is induced by the operation of the treadmill 10. The walking speed v is measured based on the speed of the belt 13 of the treadmill 10, and the walking rate p is measured based on the pressure applied to the footplate 14 of the treadmill 10 from the legs of the walking user, which improves the measurement accuracy of the walking speed v and the walking rate p.

Accordingly, it is possible to cause the user to continue the walking motion with the walking ratio $v/p^2$ kept at the target walking ratio, the walking ratio $v/p^2$ representing the relationship between the user's walking speed v and the walking rate (motion rhythm) p (or the step width (motion scale) q=v/p). This means that the walking ratio k=q/p, which is represented by tilting of the straight line $q=k_+p$, $q=k_-p$ passing through the original point on the p (waking rate)–q (step width) plane, as shown in FIG. 5, matches the target walking ratio.

Figure 5:
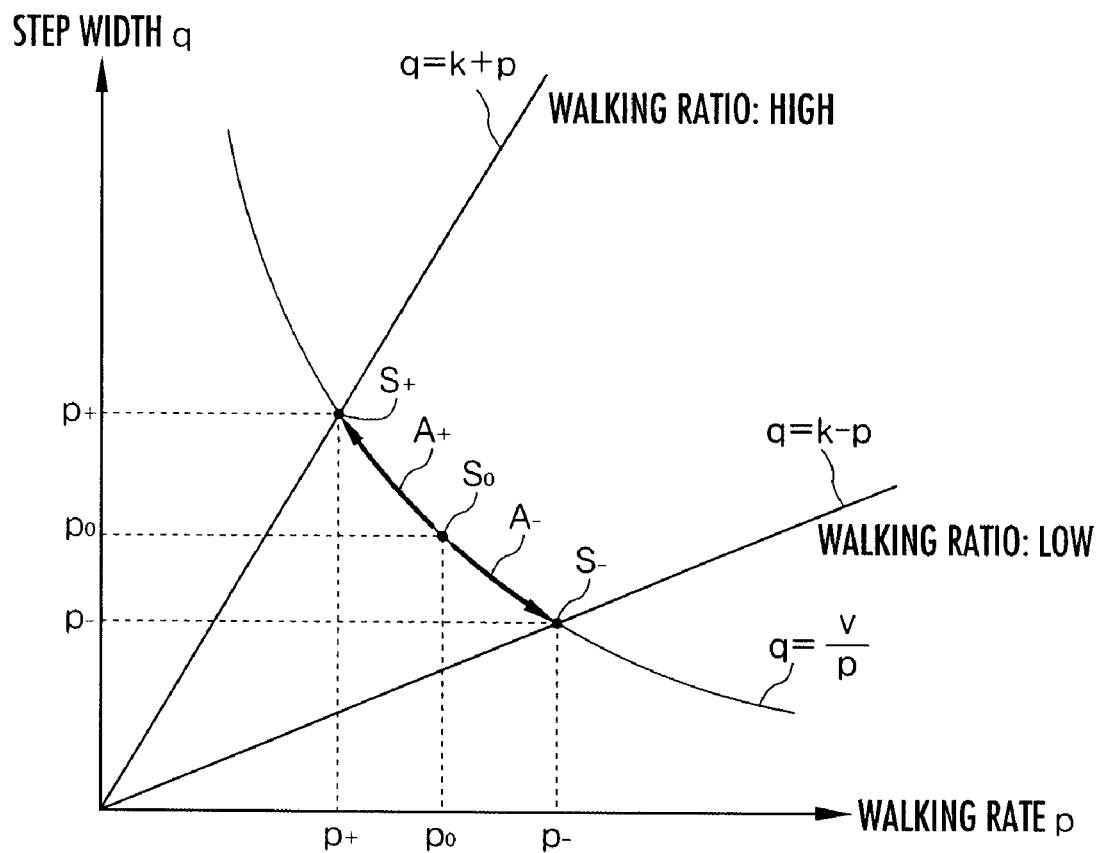
FIG. 5 is a conceptual explanatory diagram regarding the functions and effects of the exercise management system of the present invention.

Assume the case where the walking rate is adjusted from the state where the user is walking at a walking rate $p_0$ and with a step width $q_0$ represented by the point so shown in FIG. 5, for example, with the walking motion at a constant speed v ($=p_0q_0$), represented by the hyperbolic curve q=v/p, being induced by the operation of the treadmill 10.

In the case where the walking ratio represented by the tilting $k_+$ ($>q_0/p_0$) of the straight line $q=k_+p$ is set as the target, the user's motion is induced by the walking motion induction device 20 so that the user walks at the walking rate $p_+$ ($<p_0$) and with the step width $q_+$ ($>q_0$) represented by the crossing point $s_+$ of the straight line $q=k_+p$ and the hyperbolic curve q=v/p (see the arrow $A_+$ in FIG. 5). That is, the user's walking motion is gradually induced to the state where the user walks slowly in long strides, with the walking speed v kept constant.

Further, in the case where the walking ratio represented by the tilting $k_-$ ($<q_0/p_0$) of the straight line $q=k_-p$ is set as the target, the user's motion is induced by the walking motion induction device 20 so that the user walks at the walking rate $p_-$ ($>p_0$) and with the step width $q_-$ ($<q_0$) represented by the crossing point $s_-$ of the straight line $q=k_-p$ and the hyperbolic curve q=v/p (see the arrow $A_-$ in FIG. 5). This induces the user's walking motion gradually to the state where the user walks quickly in short strides, with the walking speed v kept constant.

Figure 6:
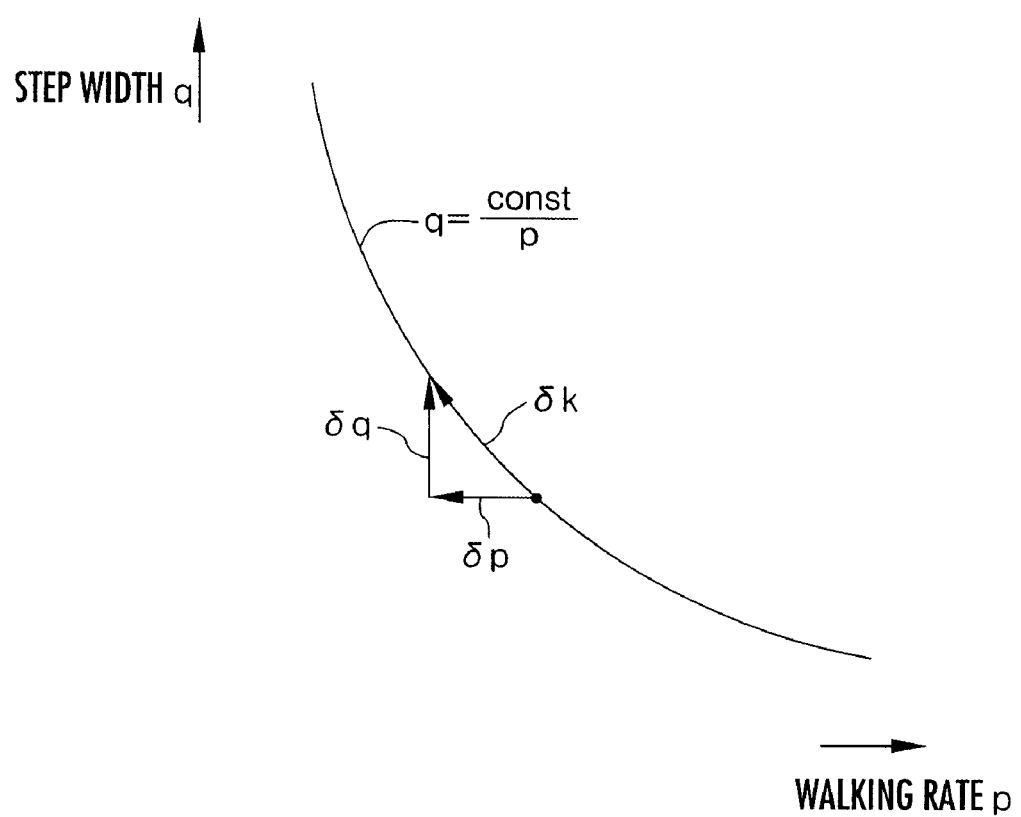
FIG. 6 is another conceptual explanatory diagram regarding the functions and effects of the exercise management system of the present invention.

While the change $\delta k$ of the walking ratio k is decomposed into the change $\delta p$ of the walking rate p and the change $\delta q$ of the step width q as shown in FIG. 6, the walking rate p and the step width q may each be changed, with harmonization established between the user's walking motion rhythm and the induction rhythm of the walking motion induction device 20 according to the induction oscillator z, for the following reasons.

The user's walking rate p may be changed to match the target walking rate, with the user's walking motion rhythm harmonized with the induction rhythm of the walking motion induction device 20 according to the induction oscillator z, for the following reasons.

The first oscillator x is generated as a signal which oscillates at an autonomous rhythm or angular velocity determined based on the natural angular velocity $\omega_M$, while being harmonized with the rhythm of the user's hip joint angular velocity (motion oscillator) $d\phi_H/dt$, by the effect of "mutual entrainment" as a property of the van der Pol equation (see the expression (1)).

The first oscillator x may have an inappropriate phase difference with the user's hip joint angular velocity $d\phi_H/dt$, from the standpoint of matching the user's walking motion rhythm with the target rhythm while harmonizing the user's walking motion rhythm with the induction rhythm of the motion by the device. As such, if the induction oscillator z is generated directly from the first oscillator x, the user's walking motion rhythm induced by the torque T around the hip joint according to this induction oscillator z may deviate from the target rhythm.

Thus, the relationship between the two virtual oscillators $\theta_h$ and $\theta_m$ is set to correspond to the phase difference (first phase difference) $\delta\theta_1$ between the user's hip joint angular velocity (first motion oscillator) $d\phi_H/dt$ and the first oscillator x. In detail, the correlation factor $\epsilon$ in the virtual model is set based on the first phase difference $\delta\theta_1$ (s233 in FIG. 2). Further, the angular velocities $\omega_h$ and $\omega_m$ of the two oscillators $\theta_h$ and $\theta_m$ are set to bring the phase difference (second phase difference) $\delta\theta_2$ between the two oscillators $\theta_h$ and $\theta_m$ close to the target phase difference $\delta\theta_d$, and the angular velocity $\omega_m$ is set as a new natural angular velocity $\omega_M$ (s234 and s235 in FIG. 2). This ensures that the new natural angular velocity $\omega_M$ becomes the angular velocity of an appropriate oscillator from the standpoint of inducing the user's walking motion to make the user's walking rate match the target walking rate, while realizing harmonization with the user's walking motion rhythm in accordance with the target phase difference $\delta\theta_d$. Thereafter, generation of the first oscillator x which periodically changes at the angular velocity determined based on the new natural angular velocity $\omega_M$ (s210 in FIG. 2) is repeated, which can gradually reduce the deviation of the first phase difference $\delta\theta_1$ from the target phase difference $\delta\theta_d$, while realizing harmonization between the rhythm of the first oscillator x and the rhythm of the motion oscillator such as the hip joint angular $\phi_H$. As such, even if the user's motion rhythm changes abruptly, it is possible to cause the induction oscillator z and the torque T to follow that change as appropriate so as not to make the user feel uncomfortable, and to cause the user's motion rhythm to gradually match the target rhythm at an appropriate pace.

Subsequently, the second oscillator $y_i$, is generated which changes over time at an angular velocity determined based on the newly set natural angular velocity $\omega_M$ (s240 in Fig. 2), and the induction oscillator z including the second oscillator $y_i$, is generated (s250 in FIG. 3). This enables a slight change of the user's walking rate p to match the target walking rate, while realizing harmonization between the user's walking motion rhythm and the induction rhythm by the walking motion induction device 20 according to the induction oscillator z. This means the harmonization (mutual adaptation) between the user (user) and the device (machine) in the form that the induction rhythm by the walking motion induction device 20 is harmonized with the user's motion rhythm and the user's motion rhythm is also harmonized with the induction rhythm by the walking motion induction device 20.

In the case where the target phase difference $\delta\theta_d$ is set to a negative value, the user can walk in the manner of leading the walking motion induction device 20. By comparison, if the target phase difference $\delta\theta_d$ is set to a positive value, the user can walk in the manner of being lead by the walking motion induction device 20.

Further, the user's step width q may be changed to match the target step width, with the user's walking motion rhythm harmonized with the induction rhythm by the walking motion induction device 20 according to the induction oscillator z, for the following reasons.

The first coefficients $g_{1+}$, $g_{1-}$ included in the first induction oscillator $z_1$ are in accordance with the first potential (potential of the virtual elastic element) for bringing the user's hip joint angle $\phi_H$ close to its target angles $\phi_{0+}$, $\phi_{0-}$. Further, the first coefficients $g_{1+}$, $g_{1-}$ are in accordance with the walking rate p and the natural angular velocity $\omega_M$ (=angular velocity $\omega_m$ of the virtual induction oscillator $\omega_m$) (see the expressions (4.1) and (4.2)). The natural angular velocity $\omega_M$ corresponds to the angular velocity of an appropriate oscillator from the standpoint of inducing the user's walking motion in such a way as to cause the user's walking rate to match the target walking rate, while realizing harmonization with the user's walking motion rhythm, as described above. Further, the target angles $\phi_{0+}$, $\phi_{0-}$ are functions of the walking speed v and the walking rate p (see the expressions (4.3) and (4.4)).

Furthermore, the second coefficients $g_{2+}$, $g_{2-}$ included in the second induction oscillator $z_2$ are in accordance with the second potential (potential of the virtual damping element) which suppresses an increase in absolute value of the hip joint angle $\phi_H$. Further, the second coefficients $g_{2+}$, $g_{2-}$ are in accordance with the walking rate p and the natural angular velocity $\omega_M$ (see the expressions (5.1) and (5.2)). The natural angular velocity $\omega_M$ corresponds to the angular velocity of an appropriate oscillator from the standpoint of inducing the user's motion to match the user's motion rhythm with the target rhythm, while realizing harmonization with the user's motion rhythm, as described above.

Thus, the first induction oscillator $z_1$ is generated in the form reflecting the first coefficients $g_{1+}(p, \omega_M)$, $g_{1-}(p, \omega_M)$ according to the walking rate p and the new natural angular velocity $\omega_M$, and the second induction oscillator $z_2$ is generated in the form reflecting the second coefficients $g_{2+}(p, \omega_M)$, $g_{2-}(p, \omega_M)$ according to the natural angular velocity $\omega_M$. This allows the user's motion to be induced in such a way as to bring the user's motion scale close to the target scale, while realizing harmonization between the user's walking motion rhythm and the rhythm of the induction oscillator z, and making the user's walking rate match the target walking rate.

Further, the target angles $\phi_{0+}$, $\phi_{0-}$ may be corrected based on the deviation of the user's measured step width (=walking speed v/walking rate p) from the target step width. The coefficients $a_{k+}$, $a_{k-}$ of the first coefficients $g_{1+}$, $g_{1-}$ and the coefficients $b_{k+}$, $b_{k-}$ of the second coefficients $g_{2+}$, $g_{2-}$ may be corrected based on the deviation of the user's measured walking rate p from the target walking rate. Furthermore, the measurement accuracy of the walking speed v and the walking rate p is improved as described above. This allows the user's motion to be induced with an appropriate rhythm and scale so that the walking ratio representing the relationship between the user's walking speed v and walking rate p matches the target walking ratio.

As described above, training of the user's walking motion is possible, by causing the user to move with a target scale and rhythm, and realizing harmonization between the user's walking motion, the operation of the treadmill 10, and the operation of the walking motion induction device 20. While the operation of the walking motion induction device 20 is controlled to make the user's walking ratio match the target walking ratio in the above example, alternatively, the operation of the walking motion induction device 20 may be controlled so that a certain relationship between the walking speed (first motion variable) v and the walking rate (second motion variable) p achieves a target relationship.

Results of experiments regarding the above-described functions and effects of the walking exercise management system 1 of the present invention will now be described with reference to FIGS. 7 to 10.

Figure 7:
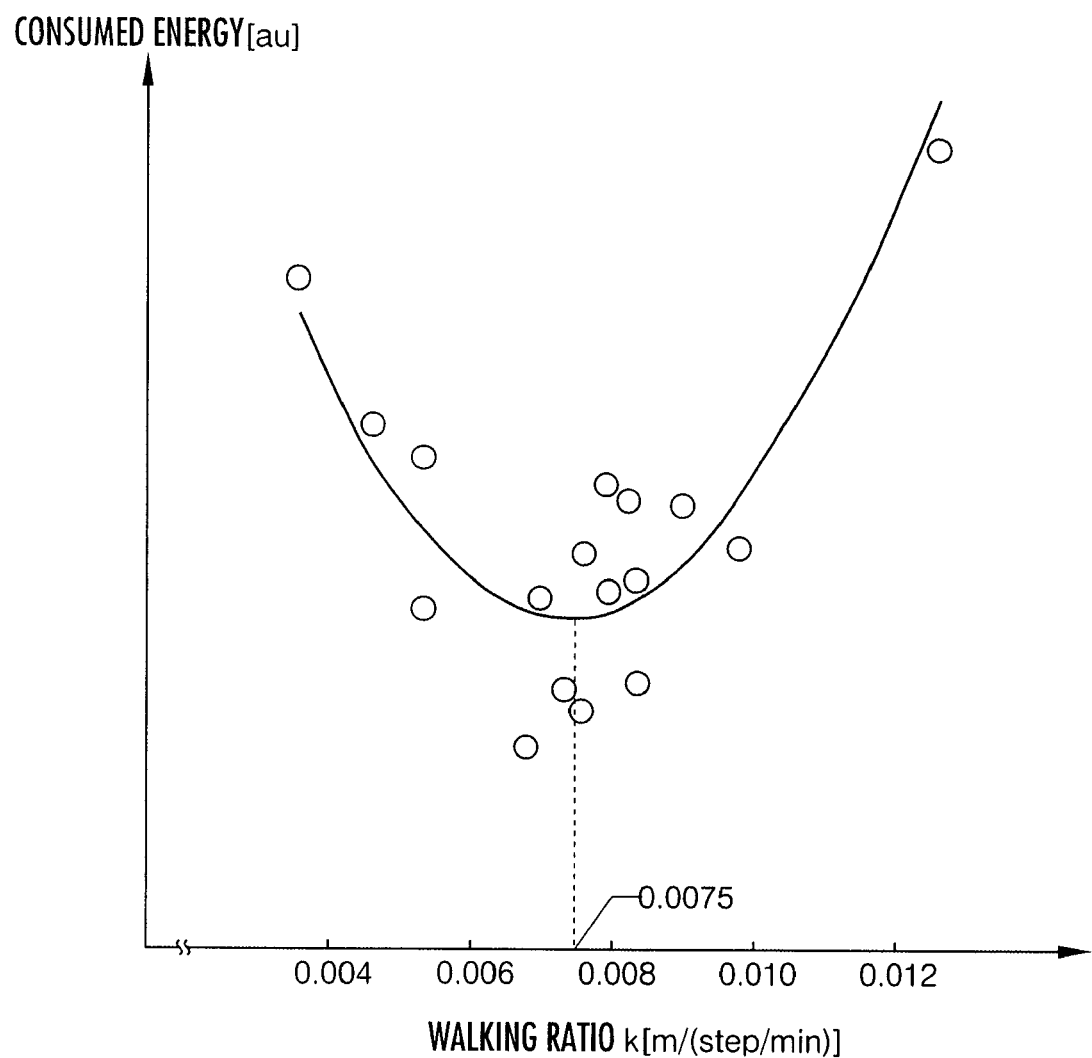
FIG. 7 is an explanatory diagram of experimental results showing the functions and effects of the exercise management system of the present invention.

Prior to the experiments, the relationship between the walking ratio k and the energy consumed by the user's walking motion was measured, which is shown in FIG. 7. Then, the walking ratio k (=0.0075) at the time when the user's consumed energy became minimal was set as a target walking ratio $k_0$, from the standpoint of alleviating the body load. It is noted that the target walking ratio may be set by the user through an operation of a setting button (not shown) provided in the walking motion induction device 20. The speed of the belt 13 of the treadmill 10 was fixed to 5 [km/s]. That is, the user's walking motion was induced by the operation of the treadmill 10 so that the user walks keeping the constant speed (5 [km/h]).

Figure 8:
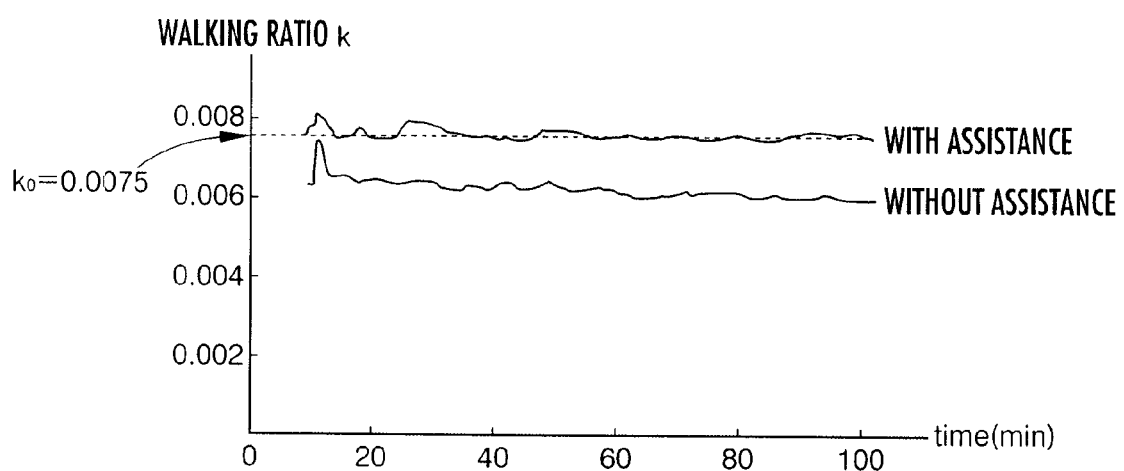
FIG. 8 is another explanatory diagram of experimental results showing the functions and effects of the exercise management system of the present invention.

As shown in FIG. 8, even if the same user walks at the same speed v, the walking ratio k varies according to whether the walking motion is induced by the walking motion induction device 20. Specifically, when the user walks without wearing the walking motion induction device 20, the walking ratio k is controlled to about 0.0065. By comparison, in the case where the user walks wearing the walking motion induction device 20 that induces the walking motion, the walking ratio k is controlled to the target walking ratio $k_{0\_}$(=0.0075) that has been set as described above. The walking motion of this user is induced by the operation of the walking motion induction device 20 so that the walking ratio k and, hence, the step width q increase. This makes it possible to train the user so that the user learns the feelings to walk at the target walking ratio $k_0$. It was confirmed that when the user walks at the speed around 5 [km/h] on a normal sidewalk or the like wearing the walking motion induction device 20, the walking ratio is maintained at the target walking ratio of 0.0075. In this manner, it is possible to train the user so that the user walks with the target step width (scale) and walking rate (rhythm).

Figure 9:
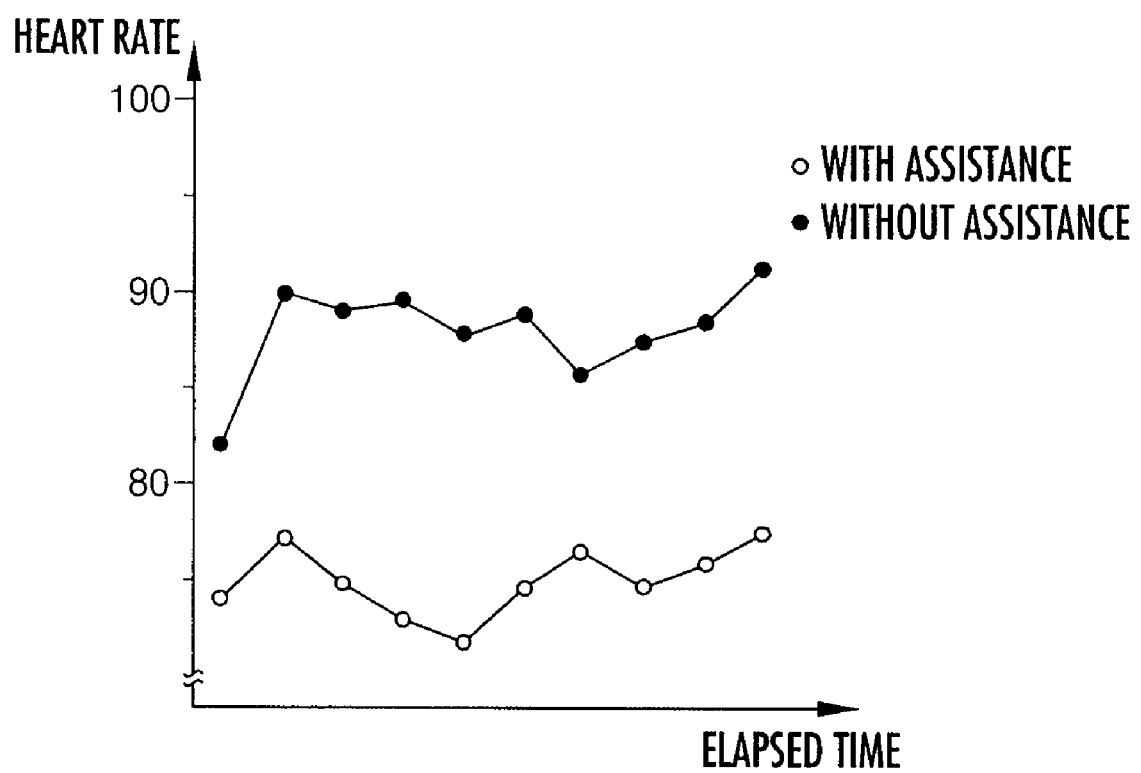
FIG. 9 is another explanatory diagram of experimental results showing the functions and effects of the exercise management system of the present invention.

Further, as shown in FIG. 9, the heart rate (physiological variable) of the same user walking at the same speed v varies depending on presence/absence of guidance of the walking motion by the walking motion induction device 20. Specifically, the heart rate when the user is walking without wearing the walking motion induction device 20 is higher than the heart rate when the user is walking wearing the walking motion induction device 20 that induces the walking motion. This means that the heart rate is restricted low and the load on the body is reduced in the state where the walking motion is induced to increase the user's step width as shown in FIG. 8.

Figure 10A:
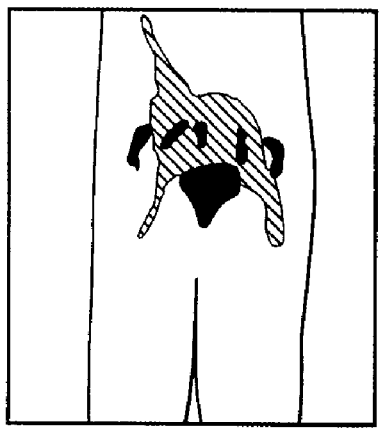
FIG. 10 is another explanatory diagram of experimental results showing the functions and effects of the exercise management system of the present invention.
Figure 10B:
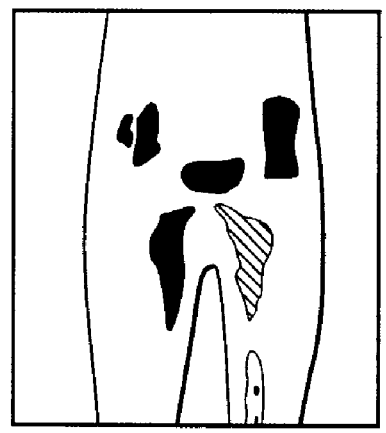

Furthermore, as shown in FIG. 10, the muscle group activity (physiological variable) in the case where the same user walks at the same speed v varies according to whether the walking motion is induced by the walking motion induction device 20. The muscle group activity around the hip joints in the case where the user is walking wearing the walking motion induction device 20 and the walking motion is induced thereby, as shown in FIG. 10(b), is higher than the muscle group activity of the same sites when the user is walking without wearing the walking motion induction device 20, as shown in FIG. 10(a). This means that the user's physical functions are activated as the user's walking motion is induced to increase the step width as shown in FIG. 8.

The results of the experiments shown in FIGS. 7 to 10 indicate the important meaning of using the exercise management system 1 for managing exercise of, e.g., the user with motor deterioration like an aged person. In other words, the use of the exercise management system 1 of the present invention suppresses degradation of, and promotes activation of, the physical functions, while reducing the body load of the aged person or the like.

Further, the user's walking or running training is possible even in a relatively small place, only if there is a space for installing the treadmill 10.

It is noted that the exercise management system 1 may be used for training of any motion other than the user's walking motion. For example, it may be used for training of the motion when the hands are used to apply forces to the left and right wheels of a wheelchair. The exercise management system 1 may also be used for training of the motion of an animal other than the human being, such as running of a horse or the like.

Moreover, for the first motion induction device, a device other than the treadmill 10 may be adopted, which induces the motion of the user's physical site, such as the leg or arm, that comes into contact with a circular motion body, by rotation of the endless circular motion body. The circular motion body may be: an endless belt looped over a plurality of rollers; a spherical body or oval sphere rotated about an axis passing the center or a point offset from the center; a tubular body such as a cylinder or square pole rotating about a central axis or an axis offset from and parallel to the central axis; or a block of substance rotated about an arbitrary axis.

In the above-described embodiment, the torques T=($T_L$, $T_R$) around the left and right hip joints in accordance with the induction oscillator z are applied to the user's body. Alternatively, the torques around various joints, such as knee joint, ankle joint, shoulder joint, elbow joint, and carpal joint, may be applied to the user's body. The combination of the joints to which the torques are to be applied may be changed for each user.

Further, in the case where the magnitude of periodical change of the hip joint angle $\phi_H$ or the hip joint angular velocity $d\phi_H/dt$ (motion oscillator) measured by the motion oscillator measuring unit 210 exceeds a threshold value, the second oscillator generating unit 240 of the second control unit 200 may generate the second oscillator y that oscillates in the rhythm reflecting one or both of the angular velocity (change of the phase over time) of, e.g., the hip joint angle $\phi_H$ measured by the motion oscillator measuring unit 210 and the angular velocity of the first oscillator x generated by the first oscillator generating unit 220, instead of the new natural angular velocity $\omega_M$ set by the natural angular velocity setting unit 230.

According to this configuration, even if the user's motion rhythm changes abruptly, the user's motion can be induced with an appropriate rhythm corresponding to the changed motion rhythm. This enables training of the user so that the user walks with an appropriate scale and rhythm, while realizing harmonization between the user's walling motion, the operation of the treadmill (first motion induction device) 10, and the operation of the walking motion induction device (second motion induction device) 20.

The induction oscillator z may be generated according to the method as disclosed in Japanese Patent Application Laid-Open No. 2004-73649.

Furthermore, the induction oscillator z may be generated in the following manner.

The motion oscillator measuring unit 210 measures motion oscillators corresponding to the user's different body parts (for example, a shoulder joint angular velocity and a hip joint angle) as a "first motion oscillator" and a "second motion oscillator", respectively. The first oscillator generating unit 220 generates a first oscillator x which attains mutual entrainment with the first motion oscillator in the form reflecting a natural angular velocity $\omega_M$. Further, the natural angular velocity setting unit 230 sets a new natural angular velocity $\omega_M$ based on the phase difference between the first motion oscillator and the first oscillator x. The second oscillator generating unit 240 generates a second oscillator y that oscillates in a rhythm reflecting the new natural angular velocity $\omega_M$, based on the second motion oscillator. Then, the induction oscillator generating unit 250 generates an induction oscillator z based on one or both of the walking speed v (first motion variable) measured by the first motion variable measuring unit 111 and the walking rate p (second motion variable) measured by the second motion variable measuring unit 112, in addition to the second oscillator y.

According to this configuration, the user's motion can be induced so that the user's motion rhythm approaches the target motion rhythm, while harmonizing the motion rhythms of the user's different body parts with the rhythm of inducing the motion. Accordingly, it is possible to train the user so that the user moves with an appropriate scale and rhythm, while realizing harmonization between the user's motion and the operations of the first and second motion induction devices.

The invention claimed is:

1. An exercise management system for managing exercise of an animal, comprising: a first motion induction device which is operative to induce motion of the animal by applying a force to the animal; a second motion induction device including a first orthosis and a second orthosis attached to the animal, an actuator mounted to the first orthosis, and a force transmitting member connected to the actuator and the second orthosis, the second motion induction device being operative to induce the motion of the animal while adjusting a motion scale and a motion rhythm of the animal with the actuator applying a force to the animal via the force transmitting member and the second orthosis; a motion variable measuring unit which measures a motion variable representing one or both of the motion scale and the motion rhythm of the animal based on an output signal from a sensor provided in the first motion induction device, in the state where the animal is moving while being induced by an operation of the first motion induction device; and a control unit which controls an operation of the second motion induction device based on the motion variable measured by the motion variable measuring unit, to induce the motion of the animal while adjusting the motion scale and the motion rhythm of the animal.

2. The exercise management system according to claim 1, wherein in the state where the motion of the animal is induced in a direction opposite from a direction in which a body part of the animal that is in contact with a rotating body provided in the first motion induction device receives a force from the rotating body with rotation of the rotating body, the motion variable measuring unit measures a first motion variable 10 as the motion variable representing a speed of the motion of the animal, based on an output signal of a speed sensor serving as the sensor that outputs a signal responsive to a rotating speed of the rotating body.

3. The exercise management system according to claim 2, wherein in the state where a walking motion of the animal is induced in a direction against the movement of an endless belt serving as the rotating body looped over a plurality of rollers provided in a treadmill serving as the first motion induction device, the motion variable measuring unit measures a walking or running speed of the animal as the first motion variable based on a driven speed of the endless belt.

4. The exercise management system according to claim 1, wherein the motion variable measuring unit further measures a second motion variable as the motion variable representing a motion rhythm of the animal, based on a pattern of change over time of an output signal of a force sensor serving as the sensor outputting a signal corresponding to a force of interaction between the animal and the first motion induction device, and the control unit controls the operation of the second motion induction device based on the second motion variable measured by the motion variable measuring unit.

5. The exercise management system according to claim 4, wherein the motion variable measuring unit measures a walking rate (corresponding to the number of steps per unit time) of the animal as the second motion variable, based on a pattern of change over time of a pressure that is applied by the animal to a footplate which supports an endless belt looped over a plurality of rollers provided in a treadmill serving as the first motion induction device.

6. The exercise management system according to claim 1, wherein the motion variable measuring unit measures a first motion variable and a second motion variable as the motion variables, by measuring a walking or running speed of the animal as the first motion variable and measuring a step width or walking rate of the animal as the second motion variable, and the control unit controls the operation of the second motion induction device so that a walking ratio matches a target walking ratio, the walking ratio being either a ratio of a square of the step width as the second motion variable with respect to the walking speed as the first motion variable, or a ratio of the walking speed as the first motion variable with respect to a square of the walking rate as the second motion variable.

7. The exercise management system according to claim 1, wherein the control unit includes: a motion oscillator measuring unit which measures a first motion oscillator and a second motion oscillator of the animal as parameters that change over time in accordance with the physical motion of the animal; a first oscillator generating unit which inputs the first motion oscillator measured by the motion oscillator measuring unit as an input oscillation signal to a first model which generates an output oscillation signal that changes over time at an angular velocity determined based on a natural angular velocity by mutual entrainment with the input oscillation signal, to generate a first oscillator as the output oscillation signal; a natural angular velocity setting unit which sets a correlation factor between a first virtual oscillator and a second virtual oscillator which are defined in a virtual model and an angular velocity of the first virtual oscillator in such a way as to cause a first phase difference corresponding to a phase difference between the first motion oscillator measured by the motion oscillator measuring unit and the first oscillator generated by the first oscillator generating unit to approach a second phase difference corresponding to a phase difference between the first virtual oscillator and the second virtual oscillator, and which sets an angular velocity of the second virtual oscillator as a new natural angular velocity in such a way as to cause the second phase difference to approach a target phase difference; a second oscillator generating unit which inputs the second motion oscillator measured by the motion oscillator measuring unit as an input oscillation signal to a second model which generates, based on the input oscillation signal, an output oscillation signal that changes over time at an angular velocity determined based on the natural angular velocity set by the natural angular velocity setting unit, to generate a second oscillator as the output oscillation signal; and an induction oscillator generating unit which generates an induction oscillator specifying a scale and rhythm of the operation of the second motion induction device, based on the motion variable measured by the motion variable measuring unit in addition to the second oscillator generated by the second oscillator generating unit, an operation of the actuator being controlled based on the induction oscillator generated by the induction oscillator generating unit.

8. The exercise management system according to claim 7, wherein the motion oscillator measuring unit measures the motion oscillator corresponding to a motion scale of the animal as a third motion oscillator, and the induction oscillator generating unit generates the induction oscillator including a first induction oscillator which represents an elastic force of a virtual elastic element for inducing the motion of the animal to cause the third motion oscillator measured by the motion oscillator measuring unit to approach a target value set in accordance with a target motion scale of the animal, based on the motion variable measured by the motion variable measuring unit in addition to the second oscillator generated by the second oscillator generating unit and the natural angular velocity set by the natural angular velocity setting unit.

9. The exercise management system according to claim 8, wherein the motion oscillator measuring unit measures the motion oscillator corresponding to a temporal differential of the third motion oscillator as a fourth motion oscillator, and the induction oscillator generating unit generates the induction oscillator including a second induction oscillator which represents a damping force of a virtual damping element for inducing the motion of the animal to suppress an increase in absolute value of the third motion oscillator, based on the motion variable measured by the motion variable measuring unit, in addition to the second oscillator generated by the second oscillator generating unit, the natural angular velocity set by the natural angular velocity setting unit, and a temporal differential of the fourth motion oscillator measured by the motion oscillator measuring unit.

10. The exercise management system according to claim 7, wherein in the case where a magnitude of periodical change of the first motion oscillator or the second motion oscillator measured by the motion oscillator measuring unit exceeds a threshold value, the second oscillator generating unit generates the second oscillator that changes over time at an angular velocity determined based on one or both of an angular velocity of the first motion oscillator or the second motion oscillator measured by the motion oscillator measuring unit and an angular velocity of the first oscillator generated by the first oscillator generating unit, instead of the natural angular velocity set by the natural angular velocity setting unit.

11. The exercise management system according to claim 7, wherein the motion oscillator measuring unit measures parameters that change over time in accordance with respective movements of two different body parts of the animal, as the first oscillator and the i0 second oscillator, respectively.

* * * * *